US009724503B2

(12) United States Patent
Khizroev et al.

(10) Patent No.: US 9,724,503 B2
(45) Date of Patent: Aug. 8, 2017

(54) ON-DEMAND DRUG RELEASE USING MAGNETO-ELECTRIC NANOPARTICLES

(71) Applicants: THE FLORIDA INTERNATIONAL UNIVERSITY BOARD OF TRUSTEES, Miami, FL (US); Ping Liang, Irvine, CA (US)

(72) Inventors: Sakhrat Khizroev, Coral Gables, FL (US); Rakesh Guduru, Miami, FL (US); Ping Liang, Carlsbad, CA (US)

(73) Assignees: THE FLORIDA INTERNATIONAL UNIVERSITY BOARD OF TRUSTEES, Miami, FL (US); Ping Liang, Irvine, CA (US)

( * ) Notice: Subject to any disclaimer, the term of this patent is extended or adjusted under 35 U.S.C. 154(b) by 246 days.

(21) Appl. No.: 14/703,521

(22) Filed: May 4, 2015

(65) Prior Publication Data

US 2016/0030724 A1 Feb. 4, 2016

Related U.S. Application Data

(63) Continuation of application No. PCT/US2013/068698, filed on Nov. 6, 2013.

(Continued)

(51) Int. Cl.

| | |
|---|---|
| ***B82Y 5/00*** | (2011.01) |
| ***A61M 37/00*** | (2006.01) |
| ***B82Y 25/00*** | (2011.01) |
| ***A61K 31/337*** | (2006.01) |
| ***A61K 9/00*** | (2006.01) |
| ***A61K 9/50*** | (2006.01) |
| ***A61K 9/51*** | (2006.01) |

(Continued)

(52) U.S. Cl.

CPC ........... *A61M 37/00* (2013.01); *A61K 9/0009* (2013.01); *A61K 9/1611* (2013.01); *A61K 9/5015* (2013.01); *A61K 9/5094* (2013.01); *A61K 9/5115* (2013.01); *A61K 9/5123* (2013.01); *A61K 9/5146* (2013.01); *A61K 31/337* (2013.01); *A61K 31/7072* (2013.01); *A61K 47/48646* (2013.01); *A61K 47/48938* (2013.01); *A61N 1/327* (2013.01); *A61N 2/002* (2013.01); *B82Y 25/00* (2013.01); *A61M 2037/0007* (2013.01); *B82Y 5/00* (2013.01)

(58) Field of Classification Search

CPC ......... A61K 31/337; B82Y 5/00; B82Y 25/00

See application file for complete search history.

(56) References Cited

U.S. PATENT DOCUMENTS

| | | | |
|---|---|---|---|
| 2004/0254419 | A1 | 12/2004 | Wang et al. |
| 2006/0142749 | A1 | 6/2006 | Ivkov |
| 2010/0284965 | A1 | 11/2010 | Fahmy et al. |

FOREIGN PATENT DOCUMENTS

| | | |
|---|---|---|
| WO | WO-00/20581 A1 | 4/2000 |

OTHER PUBLICATIONS

Hartono et al., Poly-L-lysine functionalized large pore cubic mesostructured silica nanoparticles as biocompatible carriers for gene delivery. *ACS Nano,* 6(3): 2104-17 (2012).

(Continued)

*Primary Examiner* — Carlos Azpuru

(74) *Attorney, Agent, or Firm* — Marshall, Gerstein & Borun LLP

(57) ABSTRACT

Disclosed herein are methods of delivering drugs to a subject in a controlled release fashion by administering a magneto-electric nanoparticle having ionic bonds to a drug then applying a magnetic field to weaken the ionic bonds and release the drug.

16 Claims, 14 Drawing Sheets

Related U.S. Application Data

(60) Provisional application No. 61/880,519, filed on Sep. 20, 2013, provisional application No. 61/770,695, filed on Feb. 28, 2013, provisional application No. 61/722,854, filed on Nov. 6, 2012.

(51) Int. Cl.

| | |
|---|---|
| ***A61K 31/7072*** | (2006.01) |
| ***A61N 1/32*** | (2006.01) |
| ***A61K 9/16*** | (2006.01) |
| ***A61K 47/48*** | (2006.01) |
| ***A61N 2/00*** | (2006.01) |

(56) References Cited

OTHER PUBLICATIONS

Saiyed et al., Magnetic nanoformulation of azidothymidine 5'-triphosphate for targeted delivery across the blood-brain barrier. *Intl. J. Nanomed.* 5: 157-66 (2010).
Zhen et al., Glycerol monooleate-based nanocarriers for riRNA delivery in vitro. *Molec. Pharmaceut.* 9(9): 2450-70 (2012).
International Search Report and Written Opinion of the International Searching Authority issued in connection with International Application No. PCT/US2013/068698, Russian International Searching Authority, dated Mar. 3, 2014.

A.

B.

ON-DEMAND DRUG RELEASE USING MAGNETO-ELECTRIC NANOPARTICLES

CROSS REFERENCE TO RELATED APPLICATIONS

The benefit of U.S. Ser. No. 61/722,854, filed Nov. 6, 2012; U.S. Ser. No. 61/770,695, filed Feb. 28, 2013, and 61/880,519, filed Sep. 20, 2013 are each claimed, the disclosures of which are each incorporated by reference in their entirety.

STATEMENT OF U.S. GOVERNMENTAL INTEREST

This invention was made with government support under Grant No. DA027049, awarded by the National Institutes of Health; and under grant number 005084-002 awarded by the National Science Foundation. The government has certain rights in the invention.

FIELD OF THE INVENTION

This disclosure relates to delivery and release of drugs in a controlled fashion, e.g., for delivery across the blood brain barrier (BBB), such as for HIV drugs for highly active anti-retroviral therapy (HAART), and cancer drugs, e.g., for ovarian cancer (OC) therapy.

BACKGROUND

Use of nanotechnology in medicine has shown exciting prospect for development of novel drug delivery and release system. However, existing nano-drug delivery/release strategies against HIV reservoir have less strength than limitations which restrict their use as a novel drug delivery method to CNS. For example, polymeric nanoparticles such as butyl cyanoacrylate are not ideal for the delivery of polar/ionic compounds and its degradation can produce toxic formaldehyde by-products. Polycationic surface of dendrimers is cytotoxic and associated drug release kinetics is very inconsistent. Micelles and liposomes are very unstable and possess threat of severe leakiness of associated drugs. Even drug-carrying monocytes/macrophages may have inconsistent extravasation across the BBB, and drug delivery from monocytes/macrophages may depend on exocytosis of drug containing intracellular vesicles and intracellular $Ca^{2+}$ concentrations and pathology-specific responses such as change in temperature, pH, etc. Further, magnetic nanoparticles have been used for MRI imaging purpose where ART has been tagged with specific ligands.

Earlier studies have shown that magnetic nanoparticles (MNP) tagged with AZTTP demonstrated significant inhibition of HIV-1 p24 antigen production in an in-vitro PBMC infection model system compared to free AZTTP, and magnetized monocytes containing AZTTP transmigrated across BBB by external magnetic force without affecting the integrity of BBB, although the drug release mechanism is yet to be delineated. Further, most ARV drugs have short half-life and thus their prolonged stay in periphery can remarkably reduce the active bioavailability affecting their pharmacokinetics. Most of the nanodrugs/gels reported are shown to be of more than 200 nm in size and therefore cannot penetrate through BBB. Further these drugs or drug carrying nanocarriers are also susceptible to extensive first pass metabolism or uptake by RES system. In spite of significant advances in HAART, the elimination of HIV-1 reservoirs from the CNS remains a formidable task. This is attributed to the inability of antiretroviral therapy (ART) to penetrate BBB after systematic administration. 5'-triphosphate-Azidothymidine (AZTTP), Nelfinavir, Rilpivirine, and Enfuvirtide are among the most deprived ARV drugs in the brain. Therefore, successful approach for direct and speedy delivery of these ARV drugs in sufficient therapeutic levels in the brain could pave a way for the complete eradication of HIV from the brain.

Thus existing studies showed that more than 99% of the nanodrugs are deposited either in liver, lungs or other lymphoid organs before they reach brain. So from a drug delivery point of view, a fast and effective way of delivering and releasing the drugs on demand from the carrier in the brain is very much needed to eradicate HIV reservoir or treat other CNS diseases without hampering the integrity of BBB.

SUMMARY

Provided herein are methods of administering a drug to a subject in a manner that provides controlled release of the drug. The delivery of the drug can also be targeted to a site of interest in the subject. More specifically, provided herein are methods comprising administering to a subject a plurality of magneto-electric nanoparticles (MENPs) having a drug associated thereto through an ionic bond and applying a magnetic field to the subject to weaken the ionic bond thereby releasing at least a portion of the drug from the MENP. In various cases, the MENP comprises $CoFe_2O_4@BaTiO_3$. The MENP can have a diameter of about 3 nm to about 100 nm, or about 5 nm to about 50 nm, or about 50 nm to about 1 μm. The MENP can further comprise a coating layer. The coating layer can be one or more of glycerol monooleate (GMO), polyethylene glycol, and poly-L-lysine. In some cases, the coating layer comprises GMO.

The magnetic field can arise by use of DC or AC, or a combination thereof. The strength of the magnetic field applied can be at least 10 Oe or at least 15 Oe. In various cases, the strength is about 20 to about 45 Oe, about 30 to about 35 Oe, or about 45 to about 65 Oe. The magnetic field can have a frequency of about 10 Hz to about 100 Hz, or about 500 Hz to about 1000 Hz. The methods disclosed herein provide a tailorable way to deliver the drug of interest to the subject. Choice of strength of the magnetic field and length of time the field is applied allows for a predetermined amount of drug to be released from the MENP. The amount of drug released can be at least 10%, at least 20%, at least 25%, at least 30%, at least 40%, at least 50%, at least 60%, at least 70%, at least 75%, or at least 80%. The application of the magnetic field can be performed a second time to release a second amount of drug, spaced by a desired length of time between applications of the magnetic field, for example at least 1 hour, at least 6 hours, or at least 12 hours separating the two applications of a magnetic field. The second application can be for the same amount of time as the first, or a different amount of time. It can be at the same field strength or a different (higher or lower) field strength, depending upon the amount of drug desired to be released at the second application. Whether after a single application or multiple applications, the amount of drug released to the subject can be at least 95%.

The drug delivered in the methods disclosed herein can be any drug capable of forming an ionic bond with the MENP. In some cases, the drug is an HIV or cancer drug. In various cases, the drug is AZTTP or taxol.

In various cases, the MENP can further be modified to include a chemical tagging agent. The chemical tagging agent can be used to target the MENP to the site of interest in the subject prior to application of the magnetic field. Examples include targeting antibodies and antigens (e.g., cancer antigens). The chemical tagging agent can be associated with the surface of the MENP via an ionic or covalent bond.

DETAILED DESCRIPTION

Figure 1:
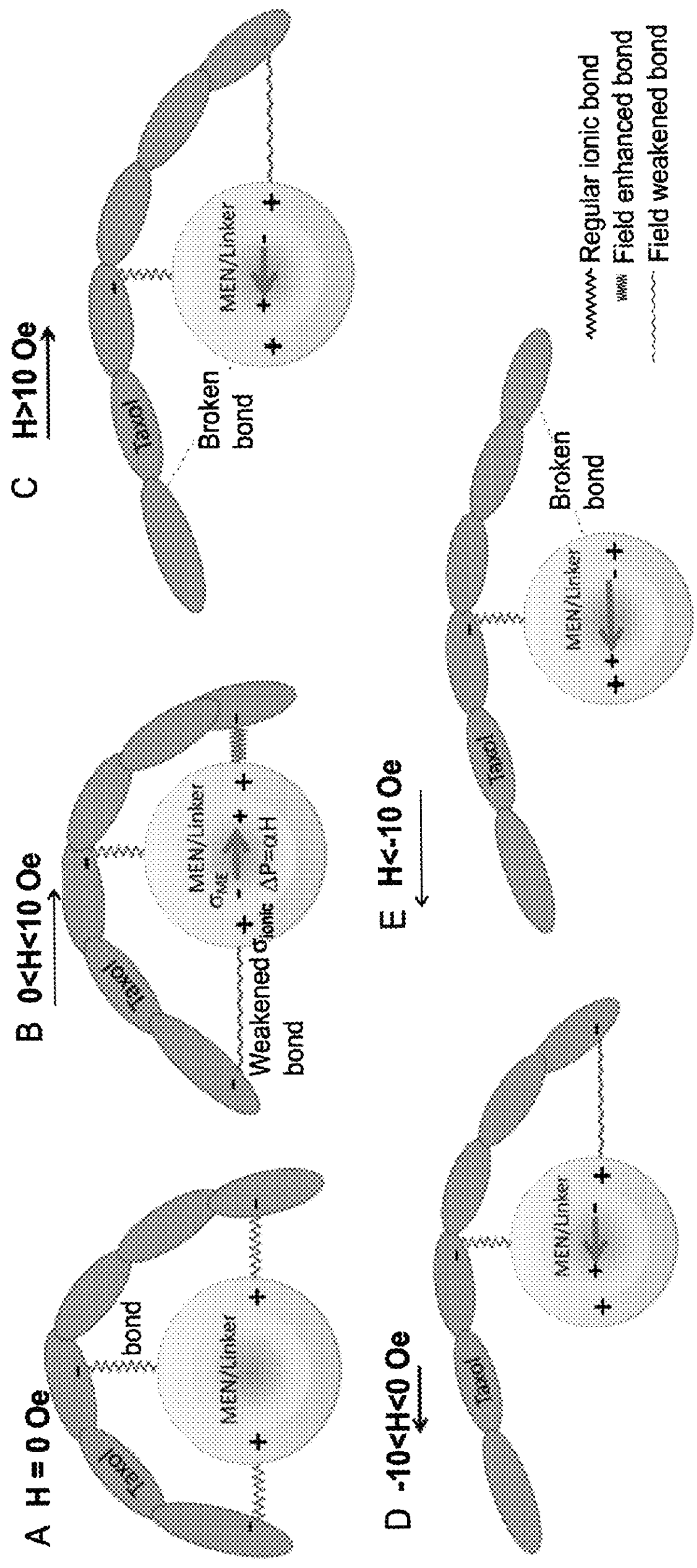
FIG. 1 shows a simplified (one-directional) illustration of the concept of on-demand drug (shown here for example only as Taxol) release by MENs stimulated by a uniform AC magnetic field in X-direction: (A) At zero field, only the ionic charge is present in the MEN shell; (B) An additional dipole moment (proportional to the magnetic field) breaks the original symmetry of the charge distribution in the shell; (C) As the field is increased above the threshold value (σionic~σME), the bond on one side is broken. (D) and (E) The field is reversed to break the bond on the opposite side of the nanoparticle. The arrows show the electric dipole due to the ME effect. In practice, due to the random configurations of nanoformulations with respect to the field, the effect is present along every central bond orientation.

The invention disclosure relates to a use of magneto-electric nanoparticles (MENPs) for on-demand drug release. These methods can be used to treat HIV, Cancer, CNS and other diseases deep in the brain and other regions of the body. MENPs belong to a new class of multifunctional nanotechnology materials that are capable of coupling between magnetic and electric fields at body temperature. The invention relies on using the unique coupling capability to enable unprecedented control (by remote magnetic field) of the electric field coupling (ionic and/or covalent) between the nanoparticle carrier and the desired drug to deliver and release the drug with record-high yield (close to 100%) on demand. The capability of MENPs to deliver drugs deep into tissues and to unleash them on demand has potential for leapfrog advances in treatment of cancer, HIV, and other CNS diseases that are considered fatal and untreatable today.

The present technology relies on chemistry to release a drug carried by a nanoparticle. As a result, the drug release yield is extremely low. For example, in case of targeted drug delivery through BBB, most of the drug carried by nanoparticles is lost as the particles are being engulfed by other cells and/or organs and consequently, less than 1% of the drug is delivered to the target. On the contrary, the invention uses a physical method of an on-demand release by MENPS (through the relatively strong coupling between remote magnetic fields and electric fields in the bond between the nanoparticle carrier and the drug).

Particularly, provided herein are methods using MENPs to achieve the following important features for drug release on-demand. First, the methods control the electric field bonding between the MENP carrier and the drug molecules (ionic and/or covalent) by magnetic (instead of electric) fields. Unlike limited to surface electric fields, magnetic fields can penetrate through the entire brain and be generated remotely. In addition, magnetic fields are less sensitive to static field and other noise sources. Second, using a magneto-electric (ME) material is a foundation that enables efficient coupling between magnetic and electric fields. Remote magnetic fields are used to induce strong electric dipole charges (in MENPs) that can significantly enhance and weaken the bond between the MENP carrier and the drug molecules. The bond, whether it is of ionic and/or covalent nature, is defined by electric fields (Coulomb forces). Therefore, each MENP serves as the nanoscale site that transfer the magnetic energy of the remote magnetic field into the electric energy of the bond between the MENP and the drug. The invented mechanism can provide almost 100% efficiency in the drug release process. For comparison, in the conventional drug delivery and release process (in which the bonding strength is controlled chemically), about 99% of the drug is lost as the nanoparticle carriers get deposited or eliminated through reticuloendothelial system (RES) before it gets across the BBB. Third, MENPs should be smaller than approximately 50 nm in diameter to penetrate the blood-brain barrier (BBB). Having the size of the nanoparticles smaller than the BBB-defined boundary, enables efficient delivery of the nanoparticles into the brain. Fourth, to control on-demand drug delivery and release using MENPs, direct current (DC) and alternating current (AC) magnetic fields are used for delivery and release, respectively.

This is the first ever attempt to couple magnetic and electric forces using MENPs (10-40 nm) to deliver bound drug, such as ART, across BBB in a noninvasive manner (by magnetic force) and forced release of bound drugs (triggered by AC electric force which in turn can be controlled by an AC magnetic field source remotely), which can be used to eradicate HIV reservoir in the brain. This new technological invention enables an unprecedented on demand drug delivery and further allows to clear the MENPs from the brain to the periphery by the reverse external DC magnetic force once the specific drugs have been released on-demand in the brain by AC triggering. Further this technology has universal applicability against variety of other CNS diseases such as Parkinson's, Alzheimer's, Huntington's disease, epilepsy, stroke, migraine headache, multiple sclerosis and brain tumors for drug targeting and release of the drug in the brain in a non-invasive manner, not to mention drug release in tissues for treatment of cancer.

Recently, we extended the proposed MENP technology to enable an on-demand drug release deep in the brain. In this case, MENPs serve as drug nano-carriers in which the strength of the ionic bonding with HIV drugs is controlled remotely by low-energy AC magnetic fields. Particularly, we used this technology to experimentally demonstrate on-demand drug release of AZTTP molecules bound to 20-nm $CoFe_2O_4$—$BaTiO_3$ MENPs. (The procedure to synthesize the MENP-drug nano-complex, further referred to as "nano-complex")

To further simplify the description, we use an example with an external magnetic field in one specific direction, e.g.

along X axis, with respect to the MENP-drug nano-complex shape. (In a practical system, there is a non-zero field component along every central orientation of the nano-complex. The analysis can be easily extended to all the other orientations.) The original (zero-field) ionic bond, with charge Qionic of the nanoparticle, is schematically illustrated (not to scale) in FIG. 1*a*. Drug molecules surround a MENP in a symmetric fashion. As shown in FIG. 1*b*, as a non-zero field is applied in X direction, a new electric dipole moment is formed in the nanoparticle due to the ME effect. According to a trivial isotropic model, the triggered moment $\Delta P=\alpha H$, where $\alpha$ is the 1st order ME coefficient and H is the magnetic field. The amplitude of the dipole charge surface density on each side of the nanoparticle would be of the order of $\sigma ME \sim \alpha H$. The dipole moment will break the original symmetry of the charge in the MENP shell. Consequently, as the magnitude of the field is increased above the threshold value at which the dipole charge density becomes comparable to the ionic charge density at the shell, $\sigma ME \sim Qionich/\pi d2$, i.e. $Hth \sim Qionich/\pi d2\alpha$, where d is the diameter of the MENP, the bond in one direction along the X axis will be broken while the opposite bond will be further strengthened, as illustrated in FIG. 1*c*. By symmetry, to break the bond in the opposite direction, the field sequence should be reversed, as illustrated in FIGS. 1*d-e*. Further, multiple field sweeps could be used to increase the drug release efficiency. The application of two-directional field sweeps to ensure high-yield drug release motivated us to use an alternating current (AC) magnetic field to enable on-demand release of the drug. The experiment described below indicated that the threshold field was of the order of 10 Oe.

Figure 2A:
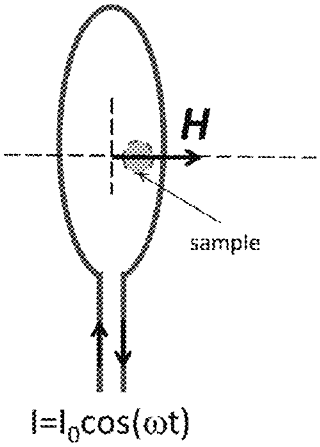
FIG. 2A-2C show schematics of applications of magnetic fields to a sample.

The most trivial setup will use only coil, as illustrated in FIG. 2*a*. The illustration is not to scale. The coil can be substantially smaller in diameter than the sample as long as it is not too far from the sample. For example, a 1000-trun coil with a 5-cm diameter can generate a field of the order of 100 Oe about 5 cm away from the center of the coil, which is sufficient to force 100% release of the drug.

However, if a specific application requires an increased energy efficiency, the following modified embodiments can be used.

Figure 2B:
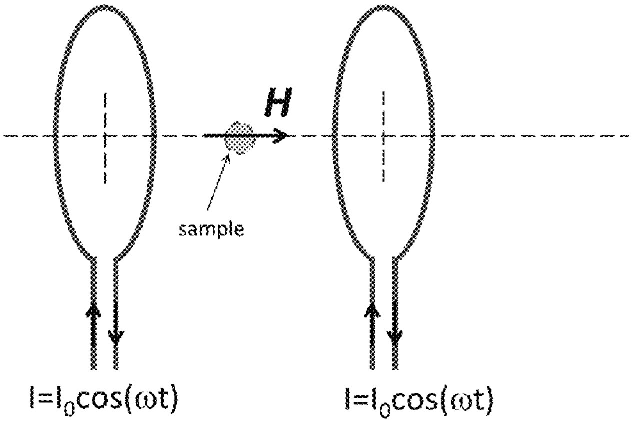

One embodiment of the technology will use a coil setup (Helmholtz pair) to generate a uniform stationary in space and varying in time AC field, as illustrated in FIG. 2*b*. This illustration is not to scale. Though the field profile is changing in time, it is stationary in space, as was the case in the previous embodiment above.

Figure 2C:
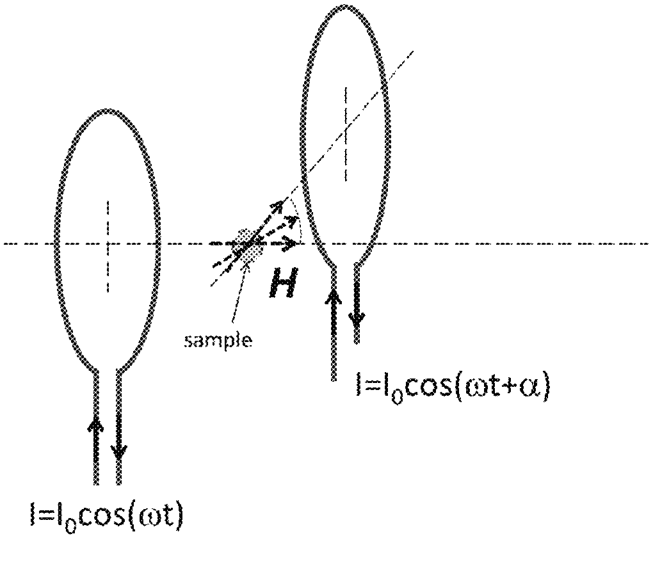

Applying an AC magnetic field that equivalently sweeps all bond orientations can create a more uniform bond-breaking process over the surface of the nanoformulation and thus enhance the drug release efficacy. In the following embodiment, this goal is achieved by using a spatially rotating field. In other words, the field profile is changing in time as well it is varying in space. The field rotation in space can be accomplished, for example, by using an array of coils that generate AC fields with non-zero phase shifts with respect to each other, as illustrated in FIG. 2*c*. Again, the illustration is not to scale. The coils don't have to be co-aligned in this embodiment. The phase shift $\alpha$ is accomplished by driving the AC electric current through the coils at the same frequency but different phase, using, for example, a phase lock-in circuitry.

Fabrication of MENPs

In general, there are many methods to fabricate MENPs. The two main approaches include chemical and physical methods. Due to the wide multidisciplinary nature of the nanoparticle applications, a review of the literature surrounding the fabrication of these particles will reveal very diverse methods of producing nanoparticles—such as thermal decomposition, co-precipitation, and many other mostly chemical processes. Most of these techniques are material sensitive chemical processes. Not every chemical composition can be easily made into nanoparticles. The ability to synthesize nanoparticles of any targeted chemical composition is also important for broadening the applications of this particular invention. Therefore, to fabricate the described MF nanoparticles, physical methods such as Ion Beam Proximity Lithography (IBPL) and Imprint Lithography might be preferred. IBPL is a unique material-independent process to fabricate nanoparticles of various compositions with a wide range of sizes (from 5 to over 100 nm) and shapes. Imprint is a state-of-the-art lithography approach suitable for mass production of features as small as 3 nm. For instance, it is hard to see how the above described chemical processes can be used to manufacture MENPs with a diameter of less than approximately 50 nm. On the contrary, with IBPL and Imprint, we can synthesize nicotine containing particles as small as 5 nm and thus cover an important nanoscale range between 3 and 50 nm. Another important advantage of a physical method is its independence of materials. Ideally, with Imprint and/or IBPL any material which could be deposited as a film, could be converted into nanoparticles. Therefore, nanoparticles of various chemical and physical properties could be fabricated economically enough for future mass production. MENP are magneto-electric materials that have no dimension greater than 5 μm, such as less than 4 μm, less than 3 μm, less than 2 μm, less than 1 μm, less than 500 nm, less than 100 nm, or are about 2 to about 15 nm. MENP include iron, cobalt, zinc, cadmium, nickel, gadolinium, chromium, copper, manganese, terbium, europium, gold, silver, platinum, oxides of any of the preceding, alloys of any of the preceding, or mixtures thereof. Specific examples of MENP include, but are not limited to, iron oxide, superparamagnetic iron oxide, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary depending on the method of synthesis. A specifically contemplated MENP is $CoFe_2O_4$—$BaTiO_3$.

Therapeutic Agents

The drug can be any therapeutic agent. Contemplated drugs include natural enzymes, proteins derived from natural sources, recombinant proteins, natural peptides, synthetic peptides, cyclic peptides, antibodies, cytotoxic agents, immunoglobins, beta-adrenergic blocking agents, calcium channel blockers, coronary vasodilators, cardiac glycosides, antiarrhythmics, cardiac sympathomimetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thiazolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-$HT_4$ partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-$A_2$ inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopeptides, lincosamides, macrolies, oxazolidinones, penicillins, streptogramins, sulfonamides, trimethoprim and derivatives, tetracyclines, anthelmintics, amebicides, biguanides, cinchona alkaloids, folic acid antagonists, quinoline derivatives, *Pneumocystis carinii* therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, anthracyclines, actinomycins, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamine reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hypnotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opioid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists. A specific class of drugs contemplated include HIV therapeutic drugs, a non-limiting example AZTTP. The drug can have a ionic moiety to form an ionic bond with the MENP (e.g., a carboxylic acid, a phosphate, a sulfonate, and/or an amine).

Field-Controlled High Specificity Drug Delivery

The nanotechnology capable of high-specificity targeted delivery of anti-neoplastic drugs would be a significant breakthrough in Cancer in general and Ovarian Cancer in particular. We addressed this challenge through a new physical concept that exploited (i) the difference in the membrane electric properties between the tumor and healthy cells and (ii) the capability of magneto-electric nanoparticles (MENs) to serve as nanosized converters of remote magnetic field energy into the MENs' intrinsic electric field energy. This capability allows to remotely control the membrane electric fields and consequently trigger high-specificity drug uptake through creation of localized nano-electroporation sites. In in-vitro studies on human ovarian carcinoma cell (SKOV-3) and healthy cell (HOMEC) lines, we applied a 30-Oe D.C. field to trigger high-specificity uptake of paclitaxel loaded on 30-nm $CoFe_2O_4$@$BaTiO_3$ MENs. The drug penetrated through the membrane and completely eradicated the tumor within 24 hours without affecting the normal cells.

The development of a technology that is capable of high-specificity targeted delivery of anti-neoplastic drugs would be a significant breakthrough in cancer in general and ovarian cancer in particular. Although the circulatory system can deliver a drug to every cell in the body, delivering the drug specifically inside the tumor cell past its membrane without affecting the healthy cells remains a challenge. In ovarian cancer, intraperitoneal (IP) delivery through a surgically implanted catheter has shown improved survival rates. However, catheter complications and toxicity have precluded widespread adoption of this invasive means of delivery. Current research attempts to go around these limiting factors by using nanoscale systems. Often, as immunological reagents, monoclonal antibodies are used to recognize the tumor-specific biomarker while the nanoscale control further improves the specificity and targeted drug delivery capability in general. Nonetheless, in spite of the tremendous progress in this field during the last decades, the capability of targeted delivery with adequately high specificity (to tumor cells) remains an important roadblock to finding a cure for cancer.

Provided herein is a study in which we address this challenge through a new physical concept. It exploits (i) the difference in the electric properties of the membrane between the tumor and healthy cells and (ii) the ability of the recently discovered body-temperature magneto-electric nanoparticles (MENs) to function as nano-converters of remotely supplied magnetic field energy into the MENs' intrinsic electric field energy. Like the conventional magnetic nanoparticles (MNs), MENs have a non-zero magnetic moment and therefore can be controlled remotely via application of an external magnetic field. However, unlike MNs, MENs offer a new far-reaching function, which is an energy-efficient control of the intrinsic electric fields within the nanoparticles by an external magnetic field. This unprecedented capability is a result of the strong magneto-electric (ME) coupling in this new class of nanostructures even at body temperature. As a result, MENs introduced in a biological microenvironment act as localized magnetic-to-electric-field nano-converters that allow remote control and generation of the electric signals that underlie the intrinsic molecular interactions. Recently, we exploited this capability: (i) to achieve remotely-controlled brain stimulation in patients with Parkinson's Disease by applying low-energy a.c. magnetic fields to control the a.c. electric signals in the central nervous system (CNS) using intravenously injected MENs and (ii) to deliver and release on-demand (via an external field) anti-retroviral (ARV) drug AZTTP for treatment of HIV-1 reservoirs across the blood brain-barrier (BBB). We exploit this capability to achieve the field-controlled specificity of the drug-loaded MENs as required to significantly improve the state of chemotherapy.

The MEN's new capability to control the local electric fields remotely (via magnetic fields) opens an exciting and previously unexplored path to exploit the intrinsic electric properties of the cell membrane. Due to the presence of ion channels and other electric-field driven properties, the cell membrane is an electrically polarizable medium. As a result, its properties can be significantly affected by an electric field. In fact, electroporation is one such well-known characteristic that exploits the dependence of the membrane's porosity on the electric field. The electroporation has been widely studied as a means to trigger drug delivery into the cells. Through macroscale studies (on samples with centimeter sizes) it is known that an electric field of higher than 1000 V/cm creates sufficiently large pores for the drug nanoformulations to penetrate through the membrane. Our new approach was to use MENs to exploit the promising delivery technique by scaling it down into the nanoscale. Due to this nano-electroporation, magnetic-field-activated MENs loaded with the drug and optionally with the biomarker-specific antibodies (for delivery to the tumor cells) can generate localized fields large enough to open up the membrane pores in their proximity only and thus let the drug inside the tumor cells. Because this process is relatively energy efficient, most of the energy goes to fulfill the main operation (of opening up the local pores, i.e. the nanoscale electroporation) and consequently it doesn't result in any significant and potentially damaging energy dissipation, e.g., in terms of heat. The interaction between the MENs and the electric system of the membrane effectively serves as a field-controlled gate to let the drug-loaded nanoparticles enter specifically the tumor cells only. An artist's view of the main hypothesis is presented in FIG. 8. In this case, the origin of the specificity to the tumor cells is two-fold. First, the biomarker-specific antibodies steer the drug-loaded MENs (to which they also are attached) to the tumor cell membrane. Second, even higher specificity is achieved due to the fact that the tumor and healthy cells have different values of the threshold field, $H_{th}$, for the "gate" to open up. Indeed, it is well-known that the electric properties differ significantly between the healthy and tumor cells of the same type. In general, the tumor cells have substantially lower values of the potential compared to that of the healthy cells. Consequently, the cancer cells must also have a significantly lower value of the threshold field for the drug-loaded MENs to enter the cell. Considering the value for the ME coefficient $\alpha$~100 mV $cm^{-1}$ $Oe^{-1}$, according to the simple isotropic expression for the ME effect, $\Delta P=\alpha H$, where P and H stand for the induced electric dipole field and the external magnetic field, respectively, the electric field of the order of 1000 V/cm can be generated a few nanometers away from the MEN merely by applying a magnetic field of 10 kOe. Moreover, the same order of magnitude electric can be generated by much smaller magnetic fields, of the order of 100 Oe, if one takes into account the pyramidal shape of the real-life nanoparticles, as shown below, because of the high-density charge accumulation at the edges. Ideally, after the drug-loaded MENs penetrate into the cell cytosol through the "open" pores in the membrane, the drug can be released off the MENs by further increasing the field above the second critical value, $H_r$, necessary for overcoming the drug-MEN binding energy. This field strongly depends on the binding force between the MEN and the drug and consequently can be tuned in a large range through using different intermediate coating materials, field excitation frequencies and treatment durations. In summary, according to our idealistic hypothesis, there are two critical field values, $H_{th}$ and $H_r$, that define the drug penetration threshold through the tumor cell membrane and the following release of the drug into the cell cytosol, respectively. To ensure adequately high efficacy of the uptake, we need $H_r > H_{th}$. To ensure the required specificity of the uptake to the cancer cells only, the external applied field, $H_A$, needs to be higher than the release field for the tumor cells, $H_{r\_cancer}$, and lower than the threshold field for the healthy cells, $H_{th\_healthy}$. In summary, using MENs not only can provide field-controlled delivery but also can significantly improve the specificity to tumor (compared to the specificity defined by the monoclonal antibodies alone). When combined, monoclonal antibodies and MENs can make even a better delivery system. While the monoclonal antibodies steer the loaded drugs towards the surface of the tumor cells, the field-controlled MENs move the drugs across the cell membrane into the cytosol.

This new high-specificity nanotechnology can be applied to the treatment of cancer in general. In the current study, to prove our hypothesis, we used Epithelial Ovarian Cancer (EOC). EOC has been widely studied in the medical community. Cytoreductive surgery followed by chemotherapy with mitotic inhibitor Paclitaxel (PTX) with platinum is the gold standard in treating EOC. In most cases, the drug administration is intravenous (IV). A less common route of administration is IP. As noted, there are technical considerations and limitations to IP therapy, although it is more effective than IV therapy. In either case, the specificity of the drug uptake is still relatively low and as a result EOC remains a highly lethal malignancy. Therefore, the current study is relevant to this field. In addition, because of the high-specificity capability, the new nanotechnology can be used for targeted treatment of both localized and metastasized tumor cells Finally, by its fundamental nature, this nanotechnology can be applied to a wide range of other cancers.

Figure 4:
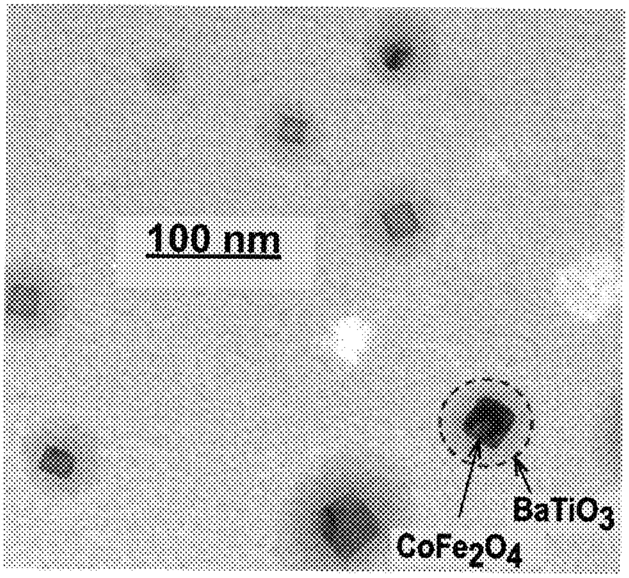
FIG. 4 shows (A) A transmission electron microscopy (TEM) image of MENs. The core-shell structure of a MEN is highlighted in red. (B) An energy-dispersive spectroscopy (EDS) analysis of MENs.
Figure 4:
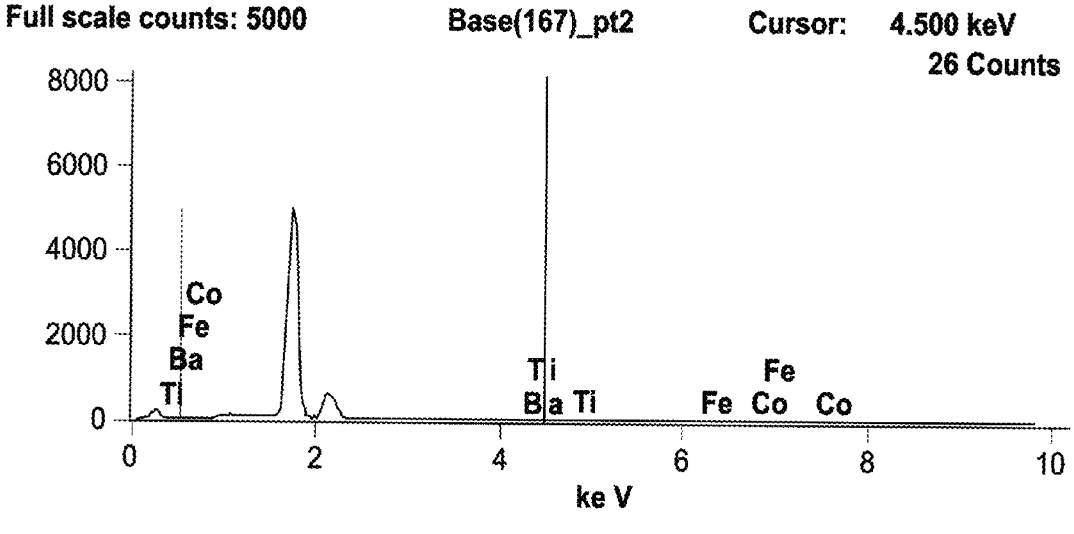
Figure 5:
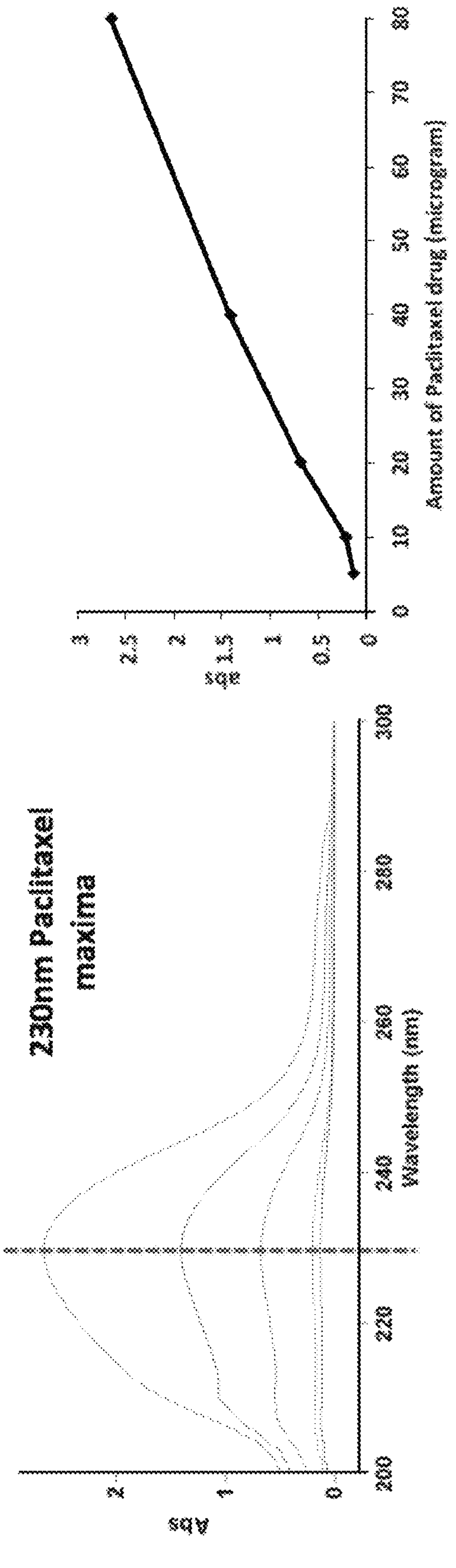
FIG. 5 shows spectrophotometry quantification (calibration) of Taxol. The calibration curve is shown on the right.
Figure 6:
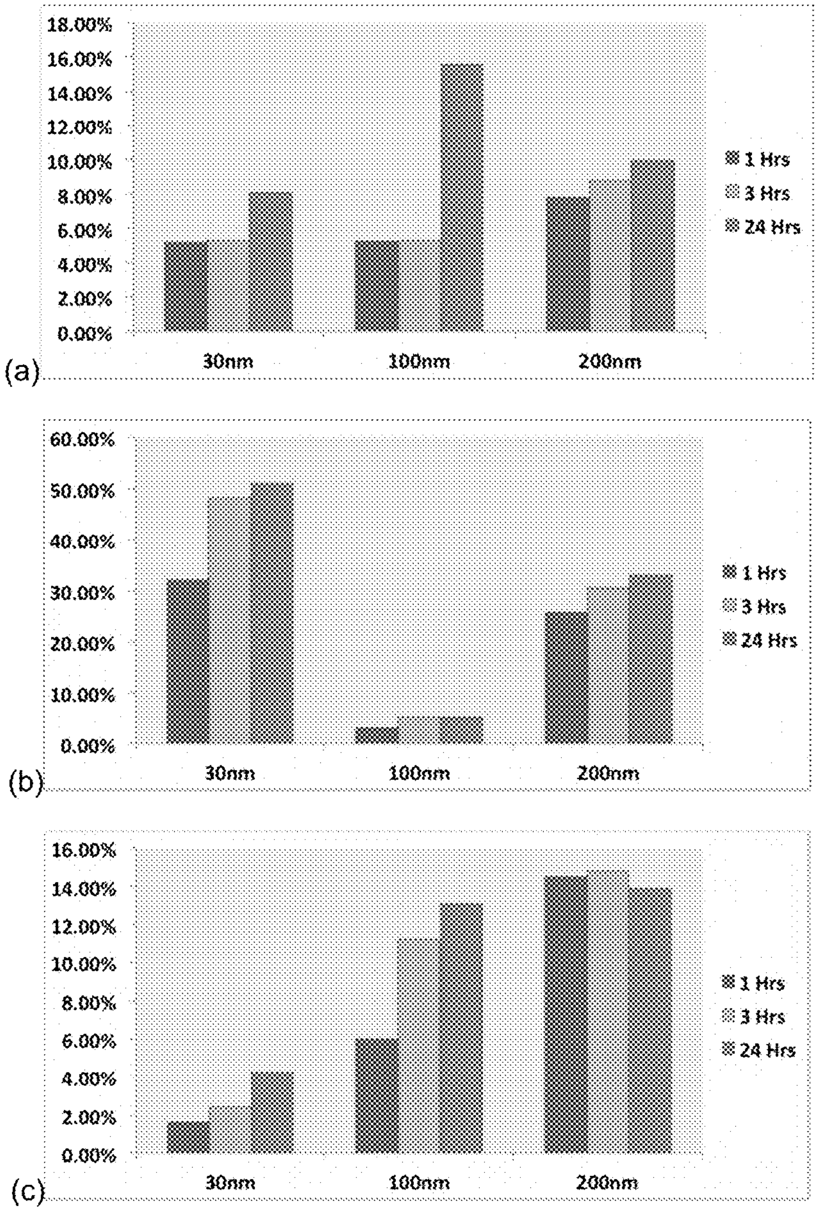
FIG. 6 shows binding results depending on the incubation conditions and size.

The results of the above experiments confirmed our hypothesis that MENs loaded with drug, e.g., PTX, can serve as high-specificity remotely controlled (via magnetic fields) delivery nanosystems to treat a particular disorder, such as EOC. We believe that this function was achieved due to the localized electroporation effects induced by the MENs in the vicinity of the cancer cell membranes when exposed to an external magnetic field. To refer to the effect at the nanoscale, we used the new terminology, "NANO-ELECTROPORATION." The experiments were conducted to separate the two core field-dependent processes according to the main hypothesis. These two processes are defined by the following two critical fields, respectively: (i) the threshold field, $H_{th}$, for MENs to penetrate through the cancer cell membrane to deliver the drug into the cell cytosol (by means of the field-induced localized nano-electroporation effect in the vicinity of MENs); and (ii) the release field, $H_r$, that triggers unloading of the drug after the drug-loaded MENs penetrated into the cell. The specificity to the cancer cells was defined not just by the typical HER-2 antibody chemistry but also by the new physical mechanism that relied on the significant difference in the threshold electric field between the healthy and cancer cells. This threshold field was measured to be of the order of 30 Oe and above 200 Oe for the SKOV-3 and HOMEC cells, respectively. Moreover, these experiments indicated that this remote-magnetic-field-triggered electric-field-defined specificity to the cancer cells resulted in a more pronounced eradication of the cancerous cells. The percentage of the cell-penetrated drug was increased by at least a factor of five compared to the traditional antibody-mediated targeting (FIG. 4). In addition, after the drug was efficiently transferred through the tumor cell membrane by the field-controlled MEN-initiated nano-electroporation, eradication of the majority of the cancer cells (without affecting the healthy cells) was observed within a 24-hour period of a low-energy 30-Oe treatment (FIGS. 5 and 6).

Figure 8:
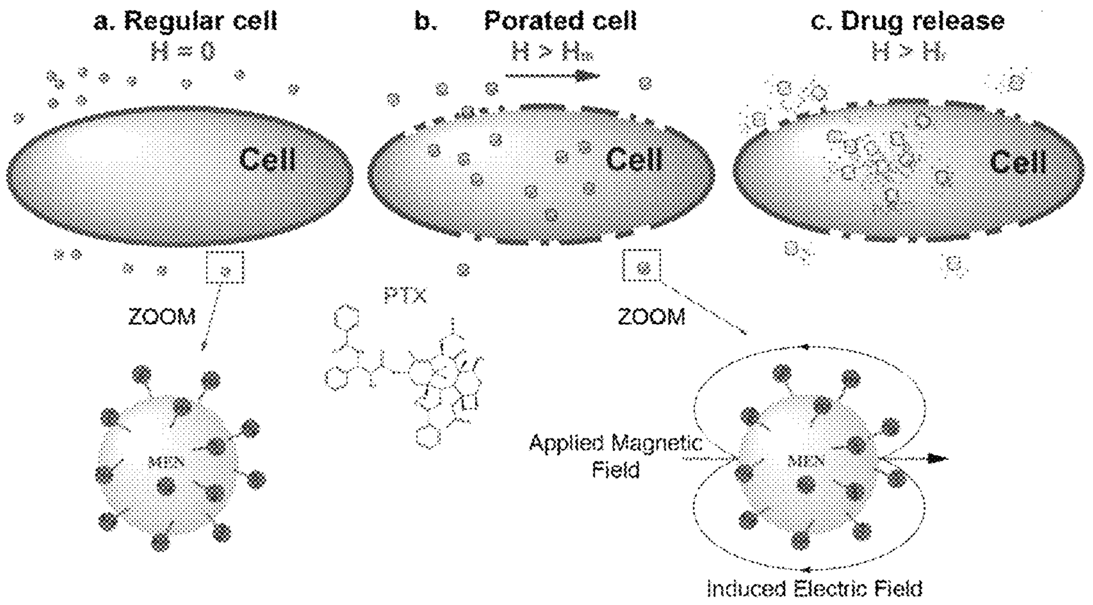
FIG. 8 shows a hypothesis illustration: MENs as field-controlled nano-electroporation sites to let the drug through the cancer cell membranes. An artist's view that illustrates how the electric medium in the cell membrane in the vicinity of MENs can effectively act as a field-controlled array of nanoscale localized gates for the drug-loaded MENs to enter the cell. The "gates", the state of which represents the degree of the membrane's porosity, are open when the remote magnetic field is above the first critical value, $H_{th}$, specific to the cell. This value for the tumor cell is at least a factor of two lower than that for the healthy cell of the same type. As the field is further increased above the second critical field, $H_r$, the release is initiated. While the release field $H_{th}$ depends on the bond between the MEN and the loaded drug molecules, the threshold field $H_{th}$ depends on the intrinsic electric properties of the membrane.
Figure 9A:
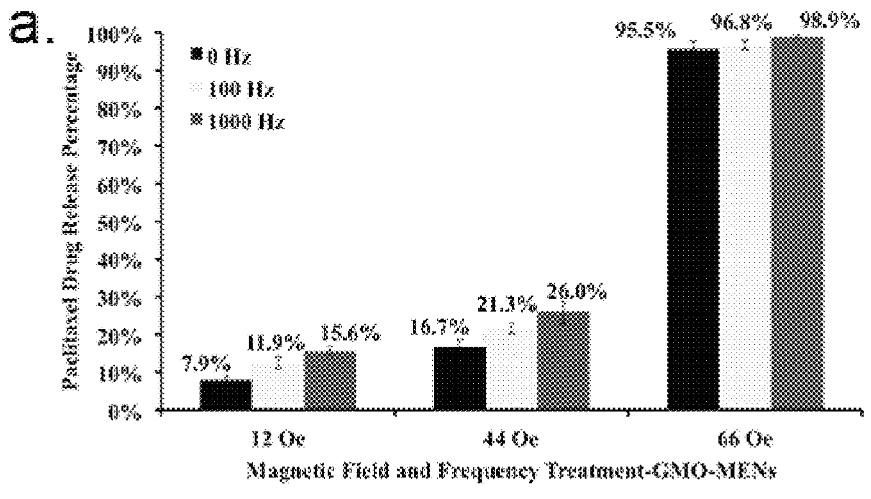
FIG. 9 (A-B) shows photo-absorption measurements of the release kinetics. (a) PTX drug release form GMO-MENs, when treated at varying magnetic field strengths and frequencies after 1-minute treatment (n=3). (b) 3-D Chart that illustrates the kinetics of the drug release. The data were measured spectrophotometrically as the absorbance at 230 nm wavelength.
Figure 9B:
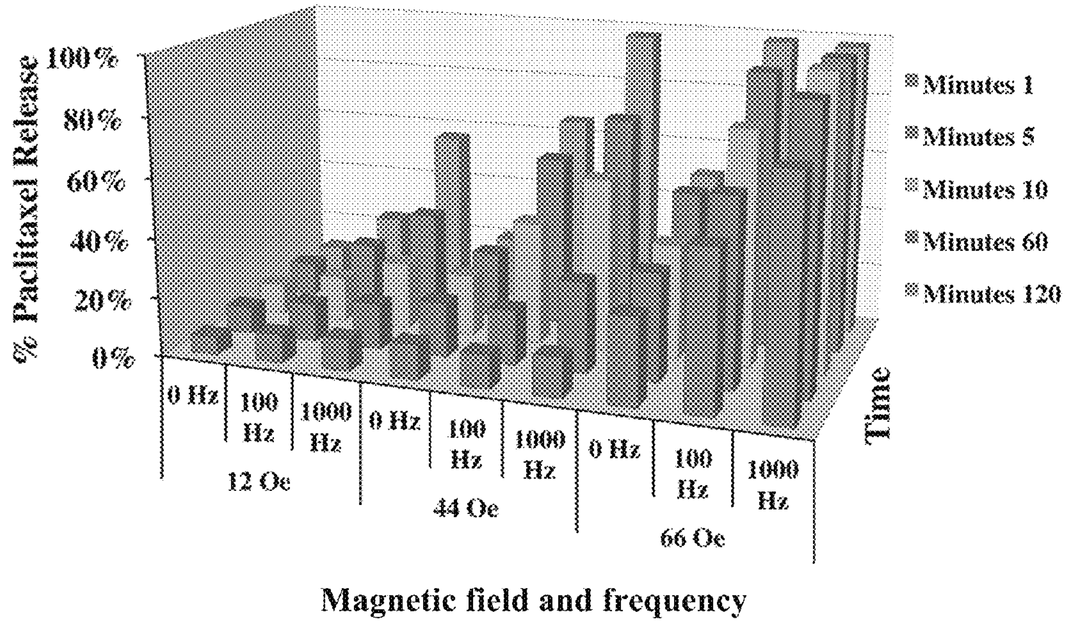
Figure 14:
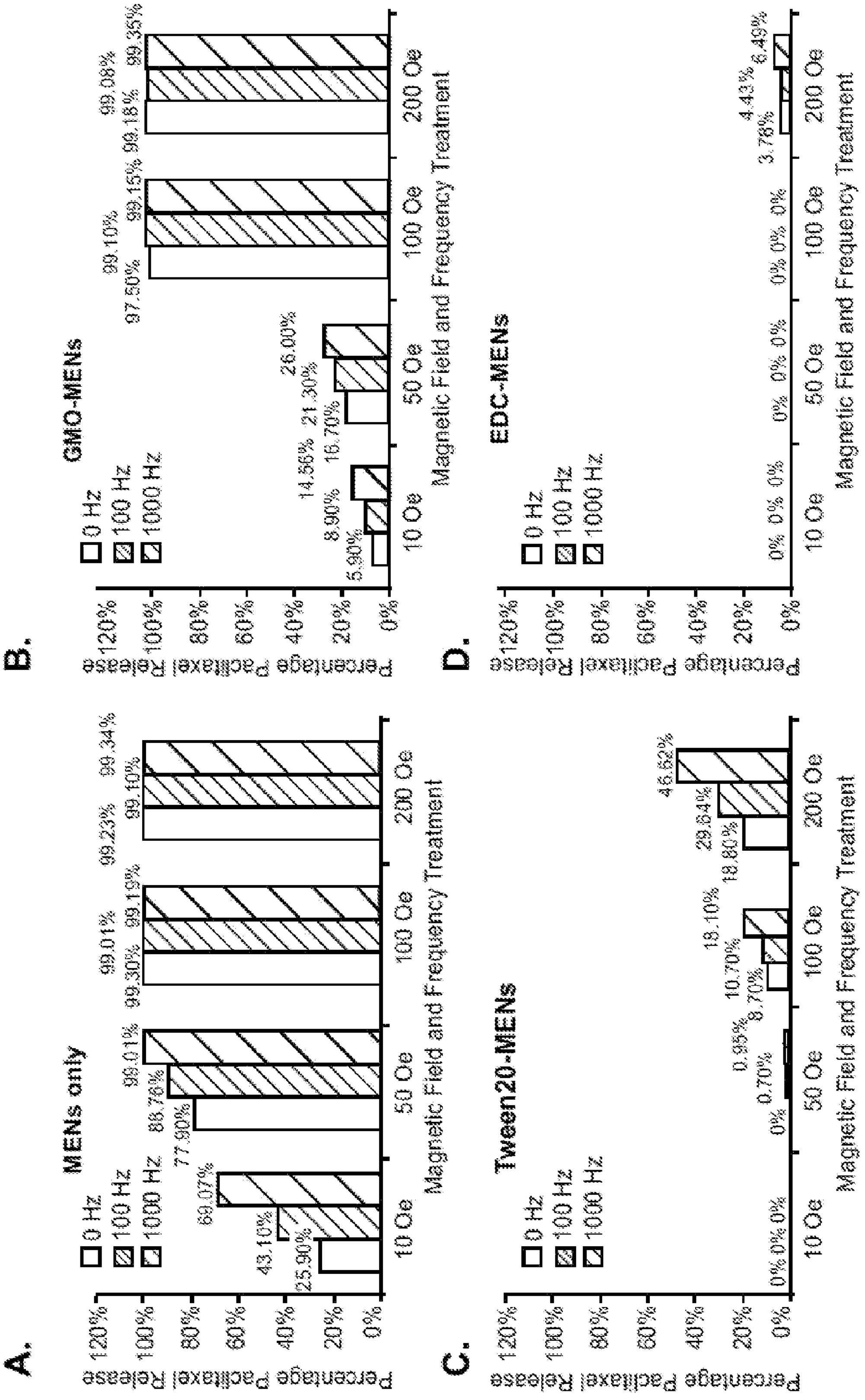
FIG. 14 shows the dependence of the release field on the intermediate layer material. The four charts show the release kinetics (field strength and frequency dependence on the field treatment duration) for (A) uncoated MENs, (B) GMO-MENs, (C) Tween20-MENs, and (D) EDC-MENs. Here EDC stands for 1-Ethyl-3-(3-dimethylaminopropyl)carbodiimide.

To achieve adequately high efficacy of the drug delivery, the value of the release field, $H_r$, was chosen to be higher than the value of the threshold field to penetrate through the membrane, $H_{th}$, for the cell of the same type. It can be reminded that the release field is defined by the binding force between the MEN and the drug, while the penetration threshold field, $H_{th}$, is mostly determined by the electric properties of the cell membrane that lead to the localized electroporation effects. We could control the release field by the proper selection of the intermediate layer between the drug and the MEN. (As summarized in FIG. 14, by choosing different intermediate layers we could control the initial release field in a wide range, from less than 10 Oe to over 200 Oe. By default, a 2-nm thin GMO layer was used as the intermediate layer.) In addition, the release field depended on the field treatment duration and the frequency of the a.c. field, as shown in FIG. 9 (bottom). For example, as shown in FIG. 9A, the spectrophotometry measurements of the absorbance at 230 nm (for PTX) indicated that only 1 minute of field treatment at a 66-Oe d.c. magnetic field was sufficient to release over 95% of the drug. As shown in FIG. 9B, the same release efficacy (of over 95%) could be achieved also at an 1000-Hz a.c. field at a smaller field strength of 44 Oe in 2 hours of treatment. This complex dependence can be explained by the fact that the external field effectively reduces the energy barrier that holds together the MEN and the drug while an increase of the treatment duration increases the temperature-induced probability to overcome the barrier or, in other words, break the bond. As for the frequency dependence, in our previous paper we explained the underlying physics through field torque effects that break the bond as the frequency increases[14]. Here, it can be mentioned that although using a.c. external magnetic fields could indeed add another knob to control the targeted delivery, in this study to focus on the proof of the main hypothesis, as illustrated in FIG. 8, we followed the d.c. field scenario. The d.c.-field-controlled drug release kinetics was confirmed also through AFM, FTIR, and Mass Spectrometry, and X-ray diffraction pattern studies. As confirmed by infrared measurements of the cellular surface temperature, the MENs's field action didn't trigger any significant temperature changes in the field and frequency range under study. This is in agreement with the fact that the MENs-induced delivery is a relatively energy-efficient process (because of the strong intrinsic magneto-electric coupling) which causes only negligible heat dissipation.

Figure 12:
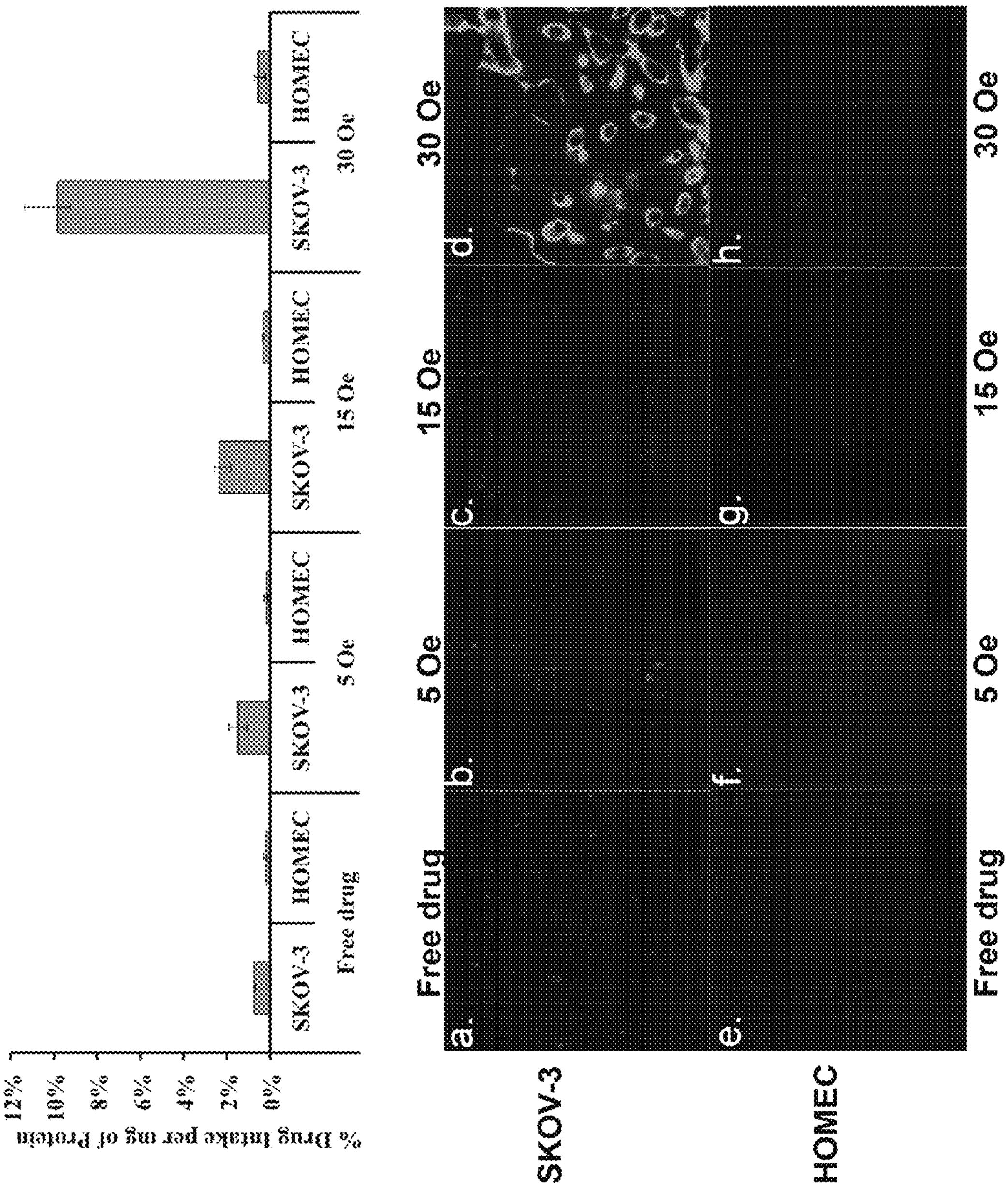
FIG. 12 shows field dependence of the drug uptake by SKOV-3 and HOMEC cells. Flutax-2 drug uptake by HOMEC (a-d) and SKOV-3 (e-h) cells with (a, e) a free drug and at in a gradually increased magnetic field of 5 (b, f), 15 (c, g), and 30 Oe (d, h). The drug uptake quantitatively presented in the top image was measured by a fluorimeter (n=3). The scale bar on the images is 47 μm.

As for the penetration threshold field, $H_{th}$, we found that for the cancer cell membrane the value was of the order of 30 Oe, i.e. less than the d.c. release field (for the default MEN carriers coated with GMO) of 60 Oe. Again, according to the main hypothesis, to ensure the specificity to the cancer cells, it is important to maintain the remote field above the release value for the tumor cells but lower than the threshold value for the healthy cells. Indeed, at a 30-Oe external d.c.

field, the drug couldn't penetrate through the healthy cell membrane for the 24-hour treatment duration, which confirmed that the threshold field for the drug-loaded MENs to penetrate into the healthy cell exceeded 30 Oe during the entire treatment (FIG. 12). Specifically, the GMO-MENs field-treated HOMEC cells showed negligible drug intake per 1 mg of the cellular protein content. The value was 0.18±0.07, 0.30±0.04, and 0.55±0.16% for the field strength of 5, 15, and 30 Oe, respectively. On the contrary, SKOV-3 cells showed significantly higher values of the drug intake, which was 1.50±0.41, 2.36±0.48, and 10.41±1.54% for the field strength of 5, 15, and 30 Oe, respectively. It can be noted that after a 24-hour 30-Oe field treatment by GMO-MENs, approximately 95 and 34% of HOMEC and SKOV-3 cells, respectively, remained viable. When the treatment was extended to 36 hours, the percentage of viable cells fell to approximately 85 and 10% for HOMEC and SKOV-3 cells, respectively. These results indicate that further field and frequency optimization could be used to perfect the treatment results.

The cytotoxicity measurements with the standard XTT assay performed on SKOV-3 cells at different concentrations of MENs showed no significant toxicity even at the highest nanoparticles concentration value of 100 μg/ml. The chart shows the results of XTT Assay performed on SKOV-3 cells at different concentrations of GMO-MENs.

The parallel study on MDR cell MES-SA/DX5 proved the applicability of the new nanotechnology to other cancers. It might be worth noting that due to the overexpressed trans-membrane proteins, e.g. P-glycoprotein, this cell type is known to be relatively impenetrable for many popular chemotherapy drugs, which makes the finding even more significant.

Through the described in-vitro studies on human ovarian carcinoma cell (SKOV-3) and healthy ovarian cell (HOMEC) lines, we demonstrated that high-specificity uptake of PTX-loaded 30-nm $CoFe_2O_4@BaTiO_3$ MENs could be triggered by a low-energy 30-Oe d.c. remote magnetic field with negligible heat dissipation. Through kinetics studies we confirmed that the drug penetrated through the tumor cell membrane and eradicated the majority of the cells within a 24-hour period without affecting the surrounding healthy cells. Finally, to demonstrate the applicability of this nanotechnology to other cancers, we conducted a parallel study using a multidrug resistant (MDR) uterine sarcoma cell type MES-SA/DX5.

The procedures to fabricate the nanoparticles with different sets of coatings and drug loadings are described in the examples. The release threshold field, $H_r$, could be controlled in a wide range, from 10 Oe to substantially over 200 Oe, through different intermediate layers/coatings. A comparative analysis of the effect of the intermediate layer type on H. is summarized in FIG. 14. By default, in order to provide adequate coupling between the MENs and Flutax-2 (to provide the initial release field of the order of 30 Oe), before being loaded with the drug, the MENs were coated with 3-Angstrom thick glycerol monooleate (GMO) layers. The zeta-potential and size of the MENs, GMO-MENs, HER2-GMO-MENs, and PTX-GMO-MENs are shown is Table 1. The Malvern Zeta-sizer was used to measures size and Zeta-potential of the MENs, GMO-MENs, HER2-GMO-MENs, and PTX-GMO-MENs (n=3). Concentration of the nanoparticles used for the measurements was 500 ug/ml of D.I water. Note: The measurements represented are the average of three independent measurements. For the purpose of a comparative analysis, we studied the following combinations of nanoparticles: (i) MENs loaded with PTX, (2) MENs loaded with PTX and the popular cancer biomarker HER-2 antibody, (3) free PTX, and (4) conventional MNs loaded with PTX. As the conventional MNs, 30-nm magnetite nanoparticles were used.

TABLE 1

| Type of measurement | Type of Particles: MENs | GMO-MENs | HER2-GMO-MENs | PTX-GMO-MENs |
|---|---|---|---|---|
| Size (nm) | 28.6 ± 7.5 | 30.9 ± 8.6 | 43.0 ± 3.6 | 44 ± 6.6 |
| Zeta-Potential (mV) | −45.0 ± 1.7 | −41.6 ± 0.3 | −26.3 ± 0.4 | −40.7 ± 0.1 |

Field-Controlled Drug Release by MEN-Based Carriers

Drug release from these different MEN-based combinations was triggered by a magnetic field at different strengths and frequencies, according to the physics described in our earlier paper on the release of ARV drug AZTTP for treatment of HIV-1 virus in the brain. The pellet obtained after the drug loading procedure was washed thrice with the phosphate-buffered saline (PBS) buffer, to remove any residual unbounded drug. The drug-loaded-MENs' pellet was added to 1 ml of the PBS buffer in a vial and subjected to a d.c. or a.c. magnetic field using a pair of Helmholtz coils connected to a d.c. or a.c. power supply, respectively. After exposing the vial to any magnetic field environment under study, the supernatant was obtained by spinning the sample at 3,000 rpm for 5 minutes and at 10° C. The supernatant was measured for the amount of the released drug spectrophotometerically through the absorbance at the PTX maximum wavelength of 230 nm.

The results of the field-controlled drug release spectrophotometry (absorption) experiments are summarized in FIG. 9. FIG. 9A shows the percentage of the drug release after a 1-minute exposure to a magnetic field at three strengths, 12, 44, and 66 Oe, respectively, for three different frequencies, 0, 100, and 1000 Hz, respectively. As expected (see explanation above), for each frequency, there was a critical field, $H_r$, at which the drug release was significantly boosted. The increase of the frequency in the range up to 1000 Hz under study increased the release efficacy (by over 40%) especially at the low field range. FIG. 9B illustrates the kinetics of the field-strength-frequency dependence of the release for the five values of the field exposure times, 1, 5, 10, 60, and 120 minutes, respectively. The quantitative values are also presented in Table 2. For every exposure time setting, a fresh solution with PTX-loaded GMO-coated MENs was used. The field-triggered drug release was also confirmed through atomic force microscopy (AFM), Fourier Transform Infra-Red (FTIR), mass spectrometry, and X-ray diffraction (XRD) pattern studies.

TABLE 2

| Field Strength | Frequency | Percentage Paclitaxel Release at Different Treatment Time Durations (Minutes): 1 | 5 | 10 | 60 | 120 |
|---|---|---|---|---|---|---|
| 12 Oe | 0 Hz | 6.1% | 9.1% | 10.3% | 11.4% | 11.1% |
| | 100 Hz | 9.5% | 12.8% | 15.3% | 20.5% | 24.4% |
| | 1000 Hz | 10.7% | 15.4% | 22.6% | 33.7% | 56.7% |
| 44 Oe | 0 Hz | 11.8% | 18.3% | 20.9% | 22.2% | 21.1% |
| | 100 Hz | 11.2% | 18.5% | 41.3% | 57.9% | 66.2% |
| | 1000 Hz | 13.4% | 30.4% | 58.2% | 73.2% | 97.8% |
| 66 Oe | 0 Hz | 29.1% | 36% | 38.4% | 49.8% | 50.5% |
| | 100 Hz | 53.1% | 62.9% | 78.5% | 92.3% | 98.5% |
| | 1000 Hz | 78.1% | 93.7% | 98.5% | 98.2% | 98.2% |

Figure 10:
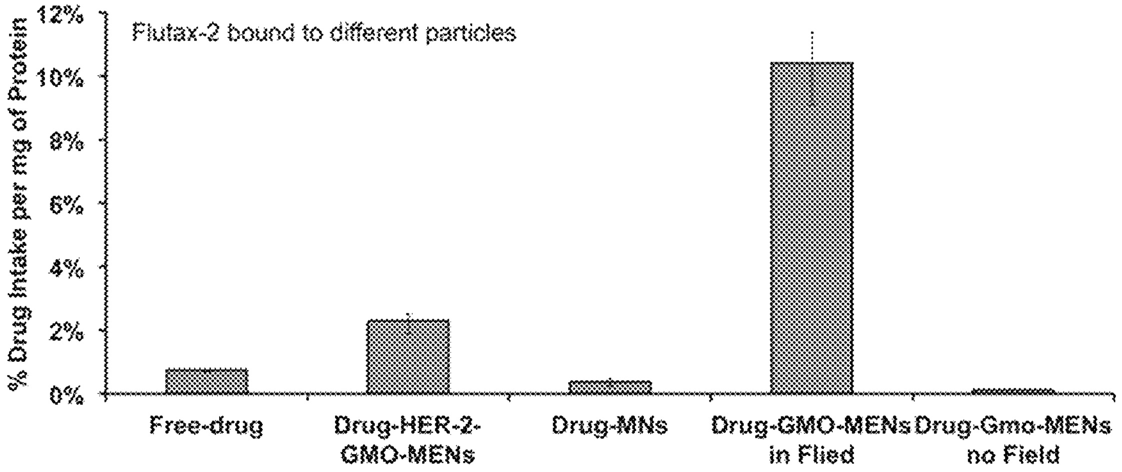
FIG. 10 shows drug uptake by cancer cells via different carriers. Comparison of four different forms of Flutax-2 drug intake by SKOV-3 cells (n=3).
Figure 11:
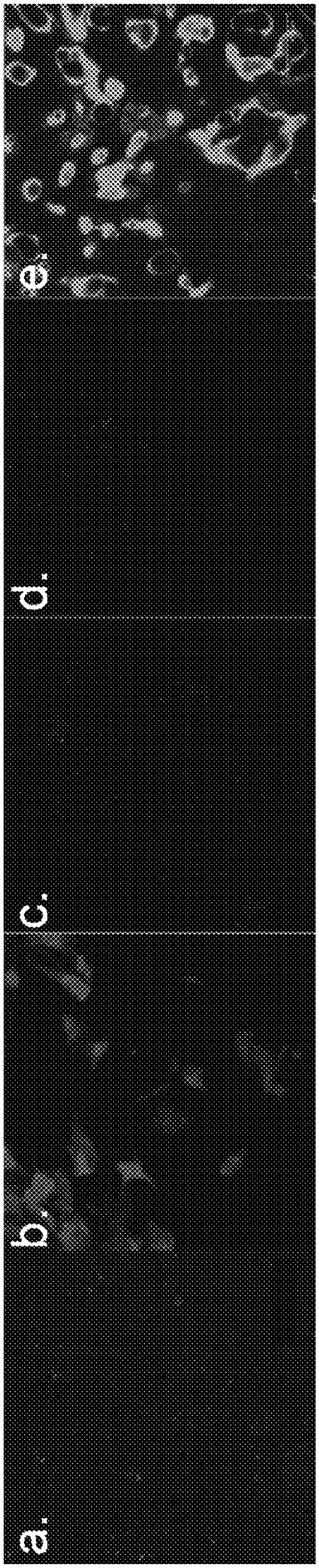
FIG. 11 shows confocal microscopy imaging of the drug uptake by SKOV-3 with different drug carriers. Confocal microscopy image of SKOV-3 cells showing the sub-localization of Flutax-2 (drug) when bound to different carrier systems: (a) free drug, (b) drug-HER-2, (c) drug-GMO-MNs in 30-Oe field. (d) drug-GMO-MENs with no field, (e) drug-GMO-MENs in 30-Oe field. The scale bar is 47 μm.

Field-Controlled Drug Uptake by Tumor Cells Through the MEN-Induced Nano-Electroporation:

Fluorescent cellular drug uptake experiments were performed on the SKOV-3 cells using the four different drug forms under study, (i) free Flutax-2, (ii) Flutax-2 bound to the conventional MNs, (iii) Flutax-2 bound to GMO-MENs, and (iv) Flutax-2 bound to HER-2-GMO-MENs, respectively. The obtained Flutax-2 concentration was normalized to the protein amount. The results of the experiment performed in triplicates are shown in FIG. 10. These results showed that the drug uptake increased by a factor of five for the drug carried by field-controlled MENs compared to the drug driven by the HER-2 antibodies.

Confocal microscopy to visualize the internal drug localization in SKOV-3 cell lines: To visualize the internal localization of each of the four drug forms under study, (i) free Flutax-2, (ii) Flutax-2-GMO-MENs, (iii) Flutax-2-HER-2, and (iv) Flutax-2-MNs, respectively, in SKOV-3 cell lines, we conducted the following fluorescence imaging experiments.

Magnetic Field Dependence of Drug Uptake in Cancer and Healthy Cells:

To understand the field dependence of the described process, we performed the cellular drug uptake experiments under a varying magnetic field strength on both cancer ovarian (SKOV-3) and healthy ovarian cell (HOMEC) lines. The HOMEC cells were cultured according to the same procedures that are described for the SKOV-3 cells in the examples. As a control, the cells with GMO-MENs only (without Flutax-2) were treated under the equivalent conditions. The cell culture plates with the MENs and drug-GMO-MENs were exposed to three different field strengths, 5, 15, and 30 Oe, respectively. The results are summarized in FIG. 12. The measurements showed that as the field was increased above approximately 30 Oe, the drug penetration into the cancer cells (SKOV-3) greatly increased. On the other hand, it can be noted that the drug barely affected the healthy cells (HOMEC) in the field range under study.

Figure 13A:
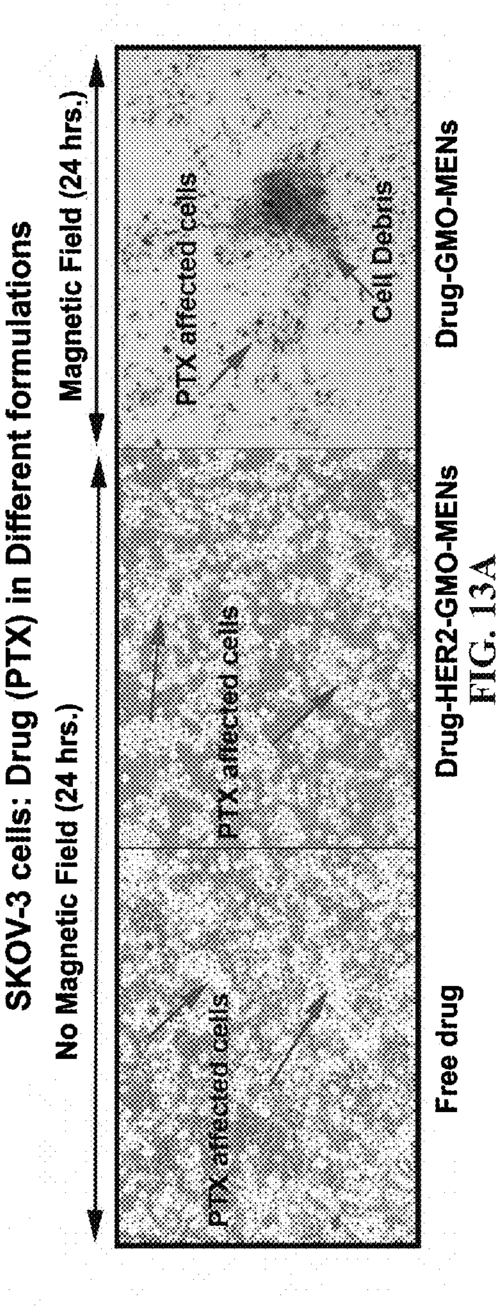
FIG. 13 (A-B) shows confocal imaging of SKOV-3 cell viability after treatment by different drug-carrier combinations with and without field. Confocal images of: (a) SKOV-3 Cells treated with PTX drug with different carrier combinations, (left) no career with no field, (middle) HER2-GMO-MENs with no field, and (right) GMO-MENs in a 30-Oe field and (b) SKOV-3 Cell Controls that include the same three carrier combinations with no PTX drug present.
Figure 13B:
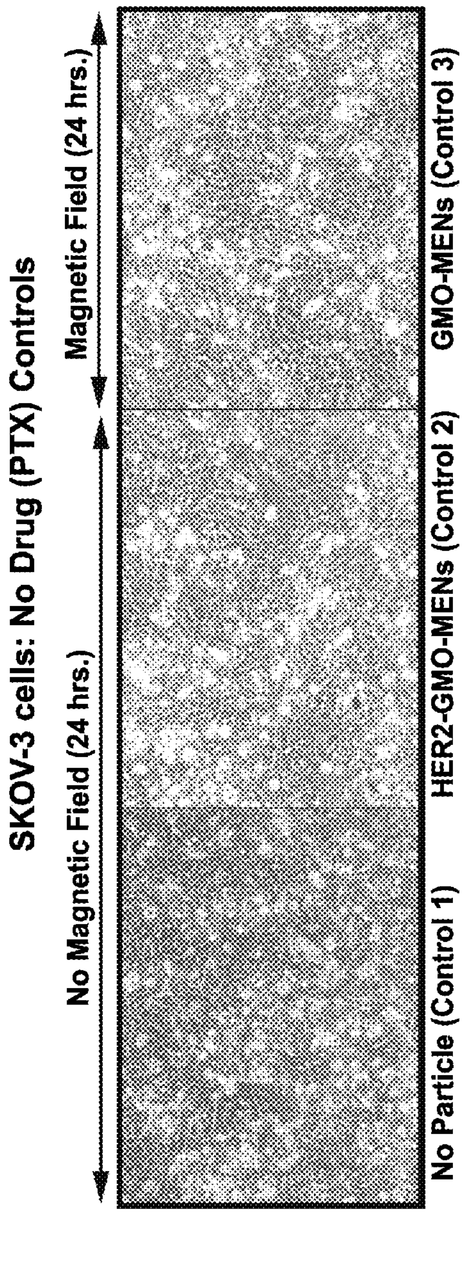

Cancer Cell Viability Test:

After we confirmed that the drug-loaded MENs in the vicinity of the cancer cells indeed acted as a field-controlled valve to let the drug in (due to the effective nano-electroporation effect according to our hypothesis), we studied the viability of the cancer cells for different combinations of the drug and the carrier after the drug penetrated through the cell membrane. (Here, maintaining the remote field at 30 Oe provided the specificity to the cancer cells or, in other words, ensured that the healthy cells were intact.) The confocal images that were obtained after a 24-hour field treatment are in FIG. 13. The three key combinations of the carrier included (i) no particle, (ii) HER-2-GMO-MENs (Note: Here, HER-2 stands for the HER-2 biomarker antibody), and (iii) GMO-MENs, respectively. Accordingly, the three images (from left to right) in FIG. 13A show the morphology of the cancer cells after 24-hour treatment by (i) the free drug (with no particle carrier), (ii) drug-HER-2-GMO-MENs with no field applied, and (iii) drug-GMO-MENs in a 30-Oe d.c. field. The three control images in FIG. 13B show the morphology of the cancer cells after the 24-hour treatment by the same three combinations of the carrier with no drug present. In addition, we conducted the confocal imaging and the trypan-blue cell viability tests on both SKOV-3 and HOMEC cell lines after 24- and 36-hour field treatment. The tryphan-blue viability data are summarized in Table 3. The table shows the percentage of SKOV-3 cells viable after the 24-hour field-treatment period for different PTX-MEN combinations and field treatment conditions (n=3). For comparison, in 24 hours, approximately 95% of HOMEC cells remain viable after the equivalent treatment by GMO-MENs at a 30-Oe field. When the treatment was extended to 36 hours, the percentage of viable cells fell to approximately 10 and 85% for SKOV-3 and HOMEC cells, respectively.

TABLE 3

| Drug | Field (30 Oe) | Type of cell | Type of Treatment | Percentage Cells Alive |
|---|---|---|---|---|
| – | – | SKOV-3 | Control-1 (No particle) | 99 ± 1% |
| | – | SKOV-3 | Control-2 (GMO-MENs-HER2) | 98 ± 1% |
| | + | SKOV-3 | Control-3 (GMO-MENs) | 98.5 ± 0.7% |
| + | – | SKOV-3 | FREE | 86 ± 8.8% |
| | – | SKOV-3 | GMO-MENS-HER2 | 71 ± 9.8% |
| | + | SKOV-3 | GMO-MENS | 31 ± 11.8% |
| | + | SKOV-3 | GMO-MENs | 33.8 ± 9.3% (24 hrs.)<br>9.7 ± 4.1% (36 hrs.) |
| | + | HOMEC | GMO-MENs | 94.9 ± 2.4% (24 hrs.)<br>84.1 ± 7.8% (36 hrs.) |

In-Vitro Cytotoxicity Assay:

To determine the cytotoxicity of the GMO-MENs on SKOV-3 cells, a quantitative colorimetric XTT (sodium 2,3,-bis(2-methoxy-4-nitro-5-sulfophenyl)-5-[(phenylamino)-carbonyl]-2H-tetrazolium inner salt) assay was performed. The assay is based on the reduction of XTT tetrazolium salt by the viable cells to form orange colored formazan derivative. In this assay, $1\times10^5$ cells were seeded per well in a 96-well plate and incubated at 37° C. for 24 hours. After the incubation, the cell medium was replaced by the medium containing the GMO-MENs at a differential concentration of 0-100 μg/ml per well and the cells were incubated for another 24-hour period. Then, the cell medium was replaced with a fresh one and washed with the PBS buffer and cell viability assay was performed by adding 50 μl per well of XTT-activated solution from the XTT test kit supplied by ATCC and incubate for 4 hours at 37° C. The experiments were performed in triplicates. No significant cytotoxicity was observed for concentrations of GMO-MENs from 0 to 100 μg/mL.

Heat-dissipation due to field-treatment with MENs: In this experiment, the temperature was measured locally via Infrared (IR) camera FLIR-i3 on the surface of both cancer (SKOV-3) and healthy (HOMEC) ovarian cells before and after a field treatment. The experimental error of the setup was approximately +/−2 Celsius degrees of the infrared camera. The magnetic field of 30 Oe was applied for a 24-hour period. No significant heat dissipation was observed as a result of the field treatment. The negligible heat dissipation (compared to the conventional method) is a consequence of the intrinsic nature of the magneto-electric coupling which resulted in the relatively high high-efficacy control of intrinsic electric fields by external magnetic fields.

Figure 15:
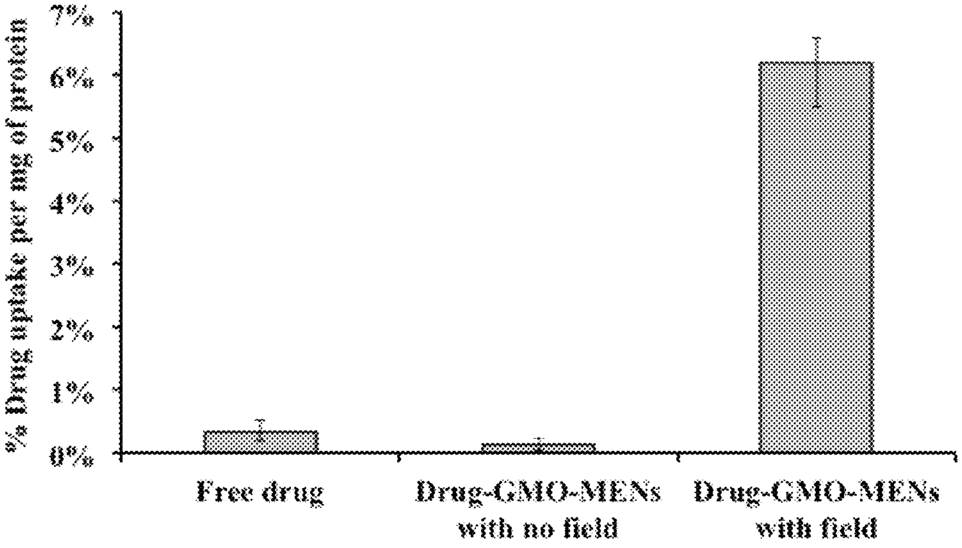
FIG. 15 shows drug uptake by MDR cells. Quantitative results of confocal microscopy imaging of the uptake of Flutax-2 by MDR cell MES-SA/DX5 for free Flutax-2, Flutax-2-GMO-MENs with no field; and Flutax-2-GMO-MENs with 30 Oe field.

Universal applicability: MENs-triggered drug uptake in MDR cell MES-SA/DX5: To demonstrate the applicability of the new nanotechnology to other cancers, we conducted a parallel study on a well-known multi-drug resistant cell line MES-SA/DX5. The results of the confocal microscopy imaging of the uptake of the same drug (Flutax-2) by this cell type is shown in FIG. 15, for free Flutax-2, Flutax-2-GMO-MENs with no field, and Flutax-2-GMO-MENs with 30 Oe field.

Model: Taxol-Based Nanotechnology for on-Demand Targeted Treatment of Ovarian Epithelial Cancer:

There are many medications/drugs associated with either of the aforementioned traditional treatment approaches. The invented nanotechnology can be used with any one or any combination of these drugs. At this early stage of the research development, we will use an Ovarian Epithelial Cancer model with drug Paclitaxel (Taxol), a popular mitotic inhibitor used in Cancer Chemotherapy in general. Other anticancer drugs can be used, with taxol merely one example. Other contemplated anticancer drugs include aspirin, sulindac, curcumin, alkylating agents, nitrogen mustard, mechlor-ethamine, cyclophosphamide, ifosfamide, melphalan, chlorambucil; nitrosourea, carmustine (BCNU), lomustine (CCNU), semustine (methyl-CCNU); ethylenimine, methylmelamine, thriethylenemelamine (TEM), triethylene, thiophosphoramide (thiotepa), hexamethylmelamine (HMM, altretamine); alkyl sulfonate, busulfan; triazine, dacarbazine (DTIC); methotrexate, trimetrexate, 5-fluorouracil, fluorodeoxyuridine, gemcitabine, cytosine arabinoside (AraC, cytarabine), 5-azacytidine, 2,2'-difluorodeoxycytidine, 6-mercaptopurine, 6-thioguanine, azathioprine, 2'-deoxycoformycin (pentostatin), erythrohydroxynonyladenine (EHNA), fludarabine phosphate, 2-chlorodeoxyadenosine (cladribine, 2-CdA); paclitaxel, a vinca alkaloid, vinblastine (VLB), vincristine, vinorelbine, taxotere, estramustine, estramustine phosphate; epipodophylotoxin, etoposide, teniposide; actimomycin D, daunomycin (rubidomycin), doxorubicin, mitoxantrone, idarubicin, bleomycins, plicamycin (mithramycin), mitomycinC, actinomycin; L-asparaginase; interferon-α, IL-2, G-CSF, GM-CSF; a platinum coordination complex, cisplatin, carboplatin, anthracenedione, mitoxantrone, hydroxyurea, N-methylhydrazine (MIH), procarbazine, an adrenocortical suppressant, mitotane (o,p'-DDD), aminoglutethimide; an adrenocorticosteroid antagonist, prednisone, dexamethasone, aminoglutethimide; progestin, hydroxyprogesterone caproate, medroxyprogesterone acetate, megestrol acetate; diethylstilbestrol, ethinyl estradiol; tamoxifen; testosterone propionate, fluoxymesterone; flutamide, leuprolide; flutamide; kinase inhibitors, histone deacetylase inhibitors, methylation inhibitors, proteasome inhibitors, telomerase inhibitor, BH3 mimetic, ubiquitin ligase inhibitor, stat inhibitor, herceptin, alemtuzumab, gemtuzumab, rituximab, ibritumomab tiuxetan, imatinib, erlotinib, cyclophosphamide, infliximab, adalimimab, basiliximab, anti CD40/CD40L antibody, anti-CTLA-4 blocking antibody, soluble LAG3 based immune modulator, MPL, CpG, single-stranded RNA, CL087, loxoribine, polyinosine-polycytidylic acid, flagellin, resiquimod, immiquimod, gardiquimod, NOD ligand, muramyl dipeptide, murabutide, peptidoglycan, muramyldipeptide, oseltamivir phosphate, Amphotericin B, palivizumab, and a combination thereof.

Unfortunately, despite its great potential the drug cannot be used to its full potential because of the existing technology limitations to achieve: (i) high-efficacy administration of the drug into the periotoneal cavity to directly target the Cancer cells and minimize exposure of normal cells; (ii) trapping and eradicating metastasized secondary cells, (iii) early-stage detection of Cancerous cells in both primary and secondary tumors. The current invention addresses the above problems in a coherent and self-consistent fashion. Particularly, the personalized nanomedicine (PNM) technology allows tailoring an optimal combination of multi-physical characteristics of nanoformulations (carriers of Paclitaxel in minutely controlled doses and capable of directly targeting selected cells) to achieve specific milestones that are highly desired for targeted treatment and diagnostics of cancerous cells.

Figure 3:
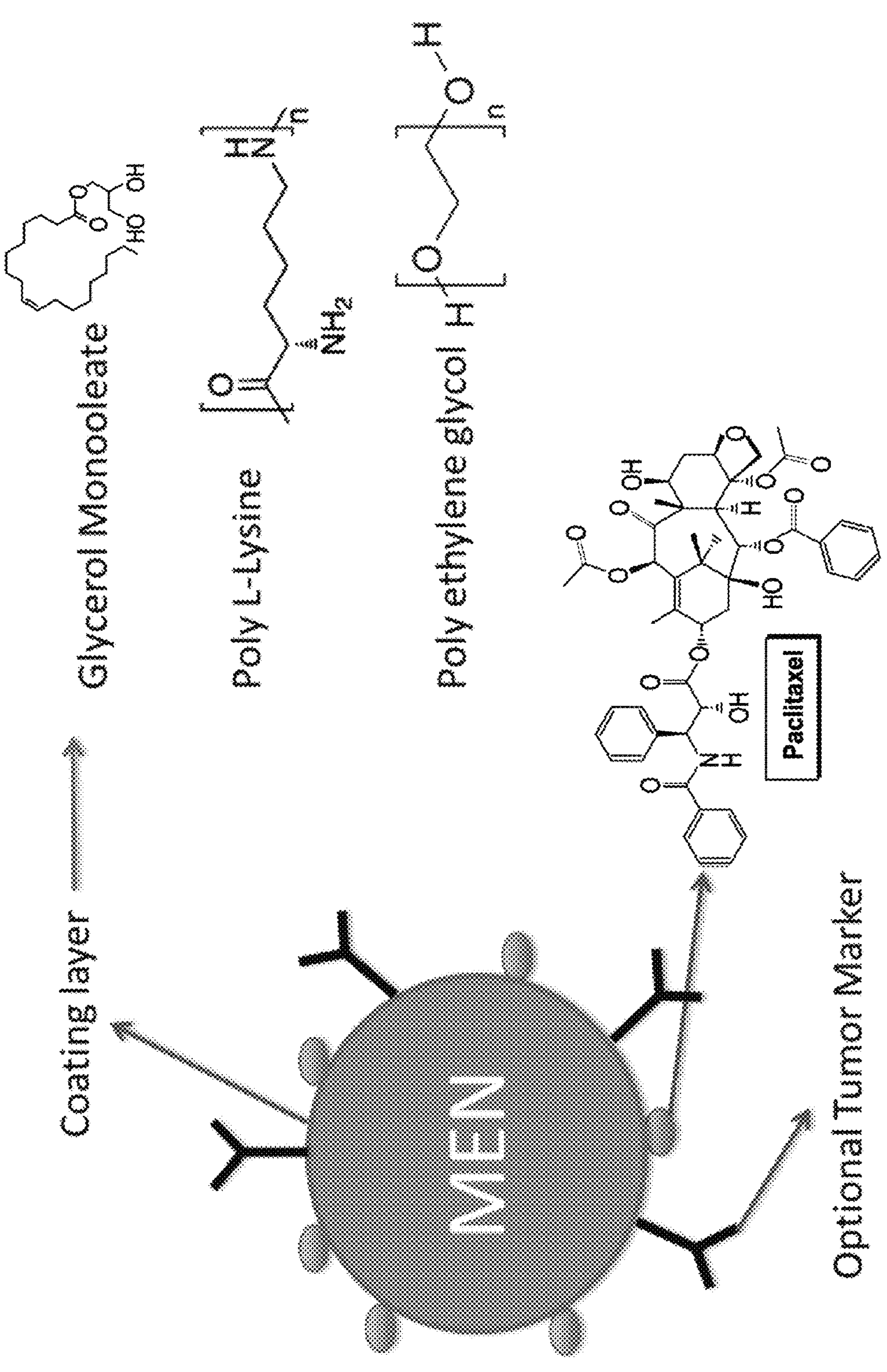
FIG. 3 shows a pictorial representation of the a product as disclosed herein: MEN-based nanoformulation that contains a drug, e.g., Taxol, and other compounds to provide a combination of diagnostics and treatment characteristics.

The main product of the invention is a magneto-electric nanoparticle (MEN) based nanoformulation, as illustrated in FIG. 3. The nanoformulation also contains Taxol and other compounds to provide the following combination of properties:

(A) Targeted physical delivery by application of a remote DC magnetic field (of less than 10 to over 100 Oe). (Such a forced (physical) delivery is especially important during treatment of “drug resistant” tumors at late stages of Cancer development. The combination of the nanoscale size and the remotely controlled (by a magnetic force) delivery allows the drug to physically penetrate the cell that otherwise would be resistant to the traditional chemical “tagging” or “marking”.) The tagging can be via inclusion of a cancer antigen on the surface of the MEN. In these embodiments, the antigen can be a tumor associated peptide or protein that induces or enhances immune response and is derived from tumor associated genes and encoded proteins including, for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, Triosephosphate isomeras, GnTV, Herv-K-mel, Lage-1, Mage-C2, NA-88, /Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, .beta.-Catenin, CDK4, Mum-1, p16, TAGE, PSMA, PSCA, CT7, telomerase, 43-9F, 5T4, 791Tgp72, .alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, and TPS. For example, antigenic peptides characteristic of tumors include those listed in International Patent Application Publication No. WO 20000/020581 and U.S. Patent Application Publication No. 2010/0284965, which are each incorporated herein by reference. In some exemplary embodiments, the antigen is a tumor antigen selected from the group consisting of MUC1, MAGE, BAGE, RAGE, CAGE, SSX-2, NY-ESO-1, PRAME, PSMA, tyrosinase, melan-A, and mixtures thereof. In some embodiments, the tumor antigen is selected from the group consisting of P1A, MUC1, MAGE-A1, MAGE-A2. MAGE-A3, MAGE-A4, MAGE-A5. MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, BAGE-1, RAGE-1, CAGE, LB33/MUM-1, NAG, MAGE-Xp2 (MAGE-B2), MAGE-Xp3 (MAGE-B3), MAGE-Xp4 (MAGE-B4), brain glycogen phosphorylase, MAGE-C1/CT7, MAGE-C2, LAGE-1, SSX-1, SSX-2 (HOM-MEL-40), SSX-3, SSX-4, SSX-5, SCP-i, NY-ESO-1, PRAME, PSMA, tyrosinase, melan-A, XAGE and mixtures thereof.

(B) On-demand (via application of an AC magnetic field) (f=10 to over 1000 Hz) high-efficacy drug release in the vicinity of or into the Cancer cells. (The sub-cellular level and extremely energy-efficient control of the drug release is enabled by the unique capability of the new nanostructures (MENs) to efficiently couple remotely generated magnetic fields with intrinsic electric charges that are involved in the covalent and/or ionic bonding between the carriers (MENs) and the drug.)

(C) Superior targeting capability because of the combined use of the physical force (via application of a magnetic field) and biological "tagging" ("marking").

(E) Precise temperature control (also known as hypothermia) at the cell level (high-frequency (above 100 KHz) AC fields). (Unlike the conventional MNs, MENs provide a very unique capability with respect to hypothermia, i.e. field-controlled hypothermia. The relatively straightforward and size- and material-selective temperature control is enabled by the unique capability of MENs to couple the magnetic spin to the electric charge. As a result, the charge distribution that strongly depends on the size and the local surrounding (of the MEN, the interface/bond, the Drug, and the bio marker) significantly affects the "heat" power (temperature) and thus provides an unprecedented and well-controlled selectivity to the size (of individual MENs) and the surrounding bio-environment.

(i) Magneto-electric Nanoparticles (MENs) can be used as nano-carriers of Taxol containing nanoformulations in a wide range of the nanoformulation diameters, from sub-10-nm to above 100 nm depending on the targeted depth of penetration. (Because MENs are used for physical (instead of chemical) targeted drug delivery, a wide range of nanoformulation sizes can be used without using relatively complex bio marking procedures.) A magnetic field in the range of less 10 to over 300 Oe is used depending on the required rate and environment of the drug administration.

(ii) Similar to conventional magnetic nanoparticles (MNs), MENs can be used for targeted delivery of Taxol. In addition, MENs can be used for high-efficacy on-demand release of Taxol deep into the tissue—one of the most critical requirements for complete eradication of OC—via application of an alternating-current (AC) low magnetic field with a magnitude of less than 100 Oe and a frequency in a 10-1000 Hz range. (MENs provide the unprecedented ability to locally convert (with almost 100% efficacy) remotely delivered magnetic energy into the molecular-level electric energy that controls bonding (ionic and/or covalent) between the MEN carrier and the drug. As a result, an unprecedented energy-efficient and high-efficacy targeted drug delivery and release can be controlled deep in the tissue.)

(iii) MENs can be further coated with various "tagging" chemicals (bio markers) to further enhance the targeting capability of the Taxol nanoformulations. In other words, the remotely controlled magnetic fields (to trigger a strong physical force required for penetration directly through the cell membrane) can be used in combination with the conventional chemical tagging to achieve superior targeting of Cancer cells.

(iv) MEN-based nanoformulations can also be used for unprecedented control of local temperature (at the sub-cellular level defined by the size of the average MEN, i.e., ranging from sub-10-nm to over 100 nm in diameter) to enable the targeted eradication of Cancer cells via "hypothermia." (The hypothermia is achieved by applying high-frequency (above 100 KHz) AC fields. Because in MENs the magnetic spin is directly coupled to the electric charge, the resonance is greatly sensitive to the size of the nanoparticles and also to the bio surrounding (the MEN, the interface/bond, the Drug, the bio marker, the tissue). We can tailor local heating to take place only in the Cancer cells in the vicinity of specified (remotely) MENs. Again, it is important to note the unique advantage of MENs (compared to conventional MNs) with regards to the capability of field-controlled Hypo-Thermia)

(v) Because MENs produce highly coupled magnetic and electric fields at the molecular level, MENs can be used to substantially improve and enable an unprecedented of any 3-D diagnostic method where today they use conventional MNs.

(vi) MENs in a wide range of sizes and shapes and compositions can be fabricated via physical nanofabrication methods such as Imprint Lithography and Ion Beam Proximity Lithography (IBPL). Optionally, conventional chemical methods can be used to fabricate MENs in a relatively narrow range of sizes and shapes and compositions.

In this invention, we exploit a previously unexplored and promising method of highly controlled on-demand release of drugs carried by nanoparticles. Specifically, we show that energy-efficient (low-field) on-demand drug release can be achieved if the conventional MN carriers are replaced by magneto-electric (ME) nanoparticles (MENs). ME materials represent a relatively recently introduced class of multi-functional nanostructures in which magnetic and electric fields can be strongly coupled even at body temperature. Similar to the traditional MNs, MENs can be designed to have adequately high magnetic moments and therefore, also can be used for targeted delivery by applying remote direct-current (DC) magnetic fields. However, unlike the traditional MNs, MENs offer an additional feature (due to their non-zero magneto-electricity) that can enable a new way to force a high-efficacy externally-controlled drug release process at the cell level using a remote alternating-current (AC) magnetic field.

The goal of this preliminary study was to demonstrate the predicted on-demand high-efficacy release of Toxil by MEN-Taxol nanoformulations. We used UV-spectrophotometry analysis in conjunction with Fourier Transform Infra-Red (FTIR) spectroscopy, mass spectroscopy, and atomic force microscopy (AFM), to directly trace the time kinetics of the drug release process at different stages of the release under the influence of remote DC and AC magnetic fields. The three key stages included (i) the initial state with separate MEN carriers and Taxol molecules, (ii) the bound state in which MEN-drug nano-formulations are formed, and (iii) the final state after AC-field-forced separation of Taxol and MENs, i.e., after the on-demand drug release. Finally, an in-vitro experiment was conducted to demonstrate the integrity of Taxol after this physical release process. Below we present the key results of this experimental study. Details of the nanoparticle synthesis and the binding chemistry are also presented.

Underlying Physics of On-demand Drug Release Using MENs as Nano-carriers: An exaggerated schematic diagram in FIG. 1 explains the concept of on-demand release of drugs from MENs. To simplify the description, we use an example with a remote magnetic field in one specific direction, e.g. along X axis, with respect to the MEN-drug nano-complex. (In a practical system, there is a non-zero field component along every central orientation of the nano-complex. The analysis can be easily expanded to all the other orientations.) The original (zero-field) ionic bond, with charge Qionic of the nanoparticle, is schematically illustrated (not to scale) in FIG. 1A. Drug molecules (typically inter-connected in chains) surround a MEN in a symmetric fashion. As shown in FIG. 1B, as a non-zero magnetic field is applied in X direction, a non-zero electric dipole moment is formed in the nanoparticle due to the non-zero ME effect. Using a simplified isotropic model, the triggered dipole moment $\Delta P=\alpha H$, where $\alpha$ is the 1st order ME coefficient and H is the magnetic field. The amplitude of the dipole charge surface density on each side of the nanoparticle along the direction of the magnetic field would be of the order of $\sigma ME\sim\pm\alpha H$, where "positive" and "negative" signs are applied to the opposite sides of the dipole, respectively. The dipole moment breaks the original symmetry of the charge in the MEN shell. Consequently, as the magnitude of the magnetic field is further increased above the threshold value at which the magnitude of the dipole charge density on the "negative" side becomes comparable to the positive ionic charge density in the shell, $\sigma ME\sim Qionic/\pi d2$, i.e. $Hth\sim Qionich/\pi d2\alpha$, where d is the diameter of the MEN, the bond in this direction along the X axis will be broken while the opposite bond will be further strengthened, as illustrated in FIG. 2C. By symmetry, to break the bond in the opposite direction, the field sequence should be repeated in the reverse direction, as illustrated in FIGS. 1D-E. This simplified scenario doesn't take into account the randomness of the orientations of the population of the nanoformulations. Ideally, applying an AC magnetic field that equivalently sweeps all bond orientations will create a more uniform and efficient bond-breaking process over the surface of the nanoformulation and thus enhance the drug release efficacy. In the next generation of the technology, this goal can be achieved by using a spatially rotating field, which in turn can be accomplished, for example, by using an array of coils that generate AC fields with non-zero phase shifts with respect to each other.

MENs:

In the experiments described below, for the role of MENs we used nanoparticles made of the popular core-shell composition $CoFe_2O_4@BaTiO_3$, in which the relatively high moment $CoFe_2O_4$ 1-nm shell was used to enhance the ME coefficient. In general, nanoparticles as small as 5-nm in diameter can be fabricated with physical methods such as ion beam proximity lithography or imprint lithography. In this study, considering the novelty of the approach, we focused on the main discovery of using MENs for on-demand drug release rather than on the development of scaling approaches. Hence, to simplify the study we used relatively large nanoparticles with diameters slightly below 50 nm. Details of the fabrication procedures are described below. A typical transmission electron microscopy (TEM) image of the fabricated MENs, with clearly visible core-shell structures, is shown in FIG. 4A. The composition of the MENs was confirmed through energy-dispersive spectroscopy (EDS), as shown in FIG. 4B. The ME coefficient for the nanoparticles was measured via point I-V methods in the presence of a field to be the order of 100 V $cm^{-1}$ $Oe^{-1}$ using an approach described in our previous publication.

Drug Binding Procedure:

2 mg of PEG/Poly-L-Lysine coated MENs nanoformulations (three different sizes of nanoformulations were used, 30 nm, 100 nm, 200 nm) were dissolved in MPBS buffer (1 ml of 70% methanol and 30% PBS solution) with 40 ug of Paclitaxel drug. The solution was incubated for 1, 3, and 24 hrs, to optimize the binding efficiency. The incubation was carried out by slowly agitating the vial to ensure uniform binding. After incubating the particles for a specific incubation time, MENs were isolated by centrifugation at 14000 rpm at 10 degree Celsius for 10 minutes. The absorbance value of supernatant was examined at 230 nm (absorbance maxima of paclitaxel reference xxx) and the binding efficiency was calculated by the below formula: "Drug loading percentage=(Absorbance of total amount of drug used−absorbance of drug used in the supernatant after incubating the drug and the MEN for a specific incubation time)×100%." The amount of drug was determined by the corresponding absorbance value spectrophotometrically using the calibration plot, as shown in FIG. 5. The drug binding results for the three sizes of the MENs, 30, 100, and 200 nm, respectively, at the three incubation durations, 1, 3, and 24 hrs, respectively, for the three different environments, with no coating at all, with Poly-L-Lysine coating, and with PEG coating, respectively, are shown in FIGS. 6*a-c*, respectively.

Magnetic field treatment: Drug conjugated MENs solution was washed once with the MPBS buffer, to make sure there is no residual unbounded drug. After, the drug-conjugated particles (paclitaxel-MENs nanoformulations) were re-dispersed in 1 ml of the MPBS buffer, and subjected to a magnetic field of varying field strength and frequency. Later, the solution was centrifuged at 14000 rpm at 10 degree Celsius for 10 minutes to isolate the supernatant. Supernatant absorbance was measured at 230 nm to determine the corresponding drug amount from the calibration curve (FIG. 5).

Figure 7:
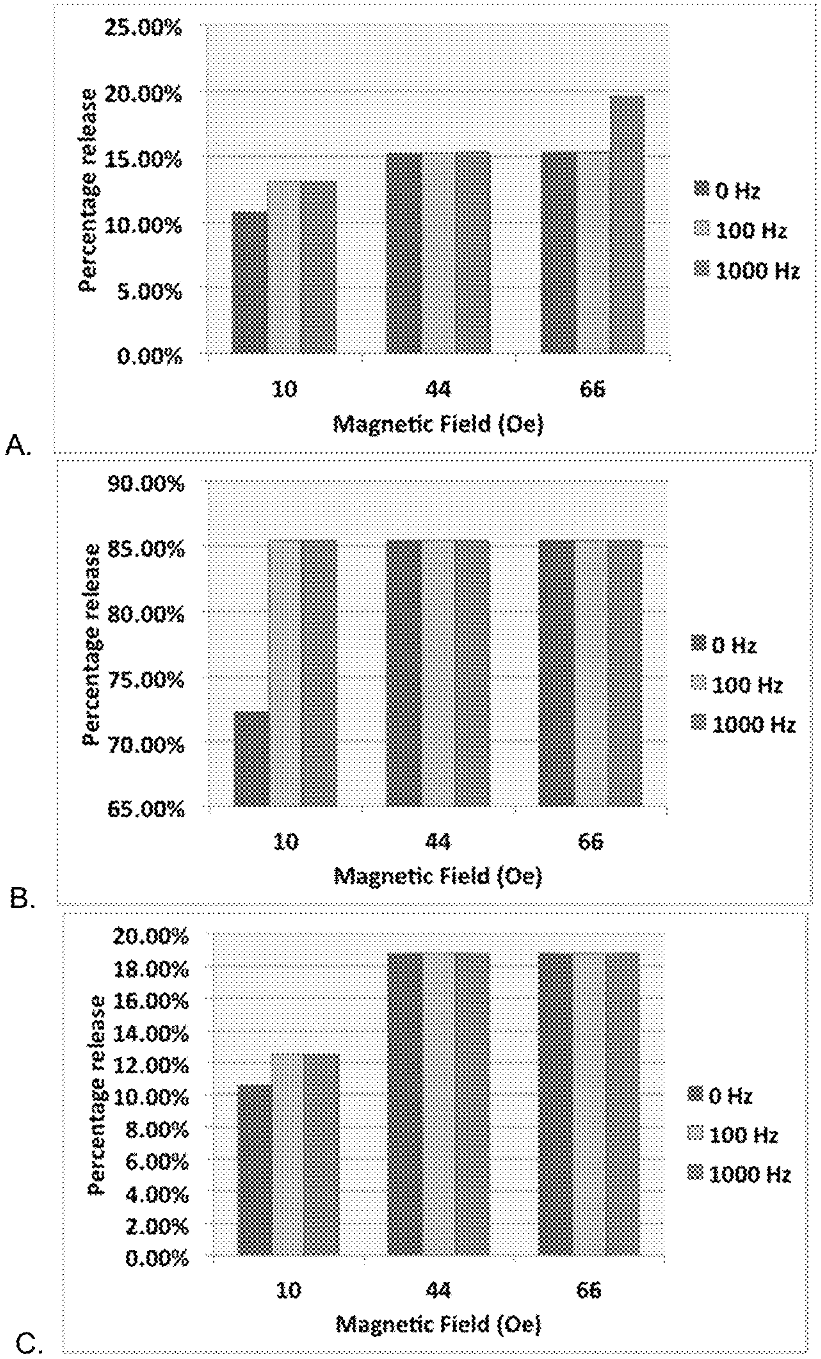
FIG. 7 shows a summary of AC-field controlled drug (Taxol) release by MENs of three different sizes: (A) 30 nm, (B) 100 nm, and (C) 200 nm.

Field-Controlled On-demand Drug Release: The drug release was only performed on Poly-Lysine coated particles, as they showed the highest binding percentage. Again, the three sizes of MENs, 30, 100, and 200 nm, respectively, were studied. The results of the field controlled Taxol release by MENs of the three sizes are summarized in FIGS. 7*a-c*, respectively. For Sample 1 (30 nm), the maximum drug release of approximately 20% was achieved at a AC magnetic field with a 66 Oe magnitude at a 1000 Hz frequency. For Sample 2 (100 nm), the maximum release of over 85% was achieved at a field amplitude of 10 Oe at a frequency of 1000 Hz. For Sample 3 (200 nm), the maximum release of over 18% was achieved at a field amplitude of 44 Oe and a frequency of 10 Hz.

EXAMPLES

Here we present the important results of a supporting experiment to demonstrate an unprecedented 100-percent yield drug release of AZTTP molecules bound to 20-nm $CoFe_2O_4$—$BaTiO_3$ MENPs by application of AC magnetic fields. 10 μl of AZTTP drug (10 mM, concentration) was added to the solution of 190 μl of TE buffer and 50 μl of $CoFe_2O_4@BaTiO_3$ coreshell nanoparticles (5 mg/ml) and later solution was incubated for 2 hrs and 3 hrs. After incubation, the solution was subjected to the magnetic field in-order to precipitate the MENPs (conjugated with AZTTP). Supernatant was isolated and its absorption was measured using spectrophotometer (Cary 100) at 267 nm.

Drug Binding Percentage: After 3 hr incubation, percentage of the drug in the supernatant was (~76%), which corresponded to 24% of the drug bound to MENPs.

| Sample | Description | Absorbance at 267 nm | % drug |
|---|---|---|---|
| 1) Only drug | AZTTP (10 µl) in 240 µl TE buffer | 0.585 | 100 |
| 3) After 3 hr Incubation | Supernatant after incubating the AZTTP drug (10 µl) with 190 µl of TE buffer and 50 µl of MENP solution (5 mg/ml concentration) for 3 hrs. | 0.445 | 76.06 |

Magnetic Field treatment: After isolating the supernatant for above measurements, the precipitate of MENPs conjugated with drug was washed once with the TE buffer, to make sure there is no residual unbounded drug. After washing the drug-conjugated particles were re-dispersed in 190 µl of the TE buffer, and subjected to the magnetic field of varying field strength and frequency. Later, the solution would precipitate to pipette out the supernatant for absorption measurements. The table below shows the absorbance measurements of supernatant after subjecting the solution to a magnetic field of varying strength and frequency.

| 12 Oe | % Drug release | 44 Oe | % Drug release | 65 Oe | % Drug release |
|---|---|---|---|---|---|
| 0 (Hz) | 1.9 | 0 (Hz) | 16.4 | 0 (Hz) | 92.9 |
| 100 | 10 | 100 | 28.5 | 100 | 97.6 |
| 1000 | 10 | 1000 | 89.28 | 1000 | |

In conclusion, at an unprecedented low field (of 65 Oe) and a frequency of 100 Hz, on-demand drug release with a yield of almost 100 percent was achieved.

Preparation of CoFe2O4-BaTiO3 Coreshell MENs:

$CoFe_2O_4$—$BaTiO_3$ core shell MENs were prepared according to the following conventional procedure. As the first step, $CoFe_2O_4$ particles were prepared by the standard hydrothermal method, according to which 0.058 g of $Co(NO_3)_2.6H_2O$ and 0.16 g of $Fe(NO_3)_3.9H_2O$ were dissolved in 15 ml of distill water and 0.2 g of polyvinylpyrrolidone was dissolved in 5 ml of aqueous solution containing 0.9 g of sodium borohydride at 120° C. for 12 hours. Then, precursor solution of $BaTiO_3$ was prepared by mixing 30 ml of aqueous solution containing 0.029 g of $BaCO_3$ and 0.1 g of citric acid with 30 ml of ethanolic solution containing 1 g of citric acid and 0.048 ml of titanium (IV) isopropoxide. Coreshell $CoFe_2O_4$—$BaTiO_3$ MENs were prepared by mixing 0.1 g of $CoFe_2O_4$ nanoparticles in the $BaTiO_3$ precursor solution and the mixture was sonicated for 2 hrs. Once the $CoFe_2O_4$ nanoparticles were thoroughly dispersed, the mixture was dried on the hot plate at 60° C. overnight while continuously stirring. The dried powder was subjected to 780° C. for 5 hrs. in a furnace (CMF-1100) and cooled at 52° C. per minute to obtained the coreshell MENs of ~30 nm diameter. The particles size distribution was measured using dynamic light scattering method (Malvern-Zetasizer).

Preparation of GMO-MENs:

In-order to load the PTX drug onto the MENs' surface, the nanoparticles were first coated with GMO to adjust the release field at about 30 Oe as required for this application. To achieve this, 1 mg of GMO was added to 5 mg of MENs in 5 ml of the PBS buffer. The mixture was then incubated for 12 hours while being slowly rotated in order to achieve uniform coating. Upon completion of the incubation process, the nanoparticles were centrifuged at 20,000 rpm for 20 minutes at 10° C. The pellet was washed in ethyl acetate:acetone (70:30) solution and re-centrifuged. The washing process was repeated thrice to completely remove the excess unbound GMO. Finally, the obtained pellet was lyophilized for 48 hours and stored for further use.

Preparation of HER-2 Biomarker Antibody Conjugated GMO-MENs:

HER-2 biomarker antibodies were covalently attached onto the GMO-MENs' surface according to the protocol as previously described. In-order to covalently attach the HER-2 antibodies, the nanoparticle surface was preliminarily functionalized. For this, 1 mg of GMO-MENs were added to 500 µl of the PBS buffer (pH 7.4). To this solution, 25 µl of N-(3-Dimethylaminopropyl)-N'-ethyl-carbodiimide hydrochloride (EDC) and 25 µl of N-hydroxysuccinimide (NHS), at 1 mg/ml concentration in the PBS buffer (pH 7.4) were added. The solution was incubated for 4 hours at room temperature while being stirred slowly. Then, the sample was centrifuged at 14,000 rpm for 10 minutes at 10° C. and the pellet was washed three times with 1 ml of the PBS buffer (pH 7.4). To bind HER-2 antibodies to the functionalized MENs, 10 µl of the antibodies (1 mg/ml) was added to the pellet along with 300 µl of the PBS buffer (pH 7.4). The solution was incubated for 2 hours while being rotated slowly and kept further at 4° C. overnight. The solution was centrifuged at 14,000 rpm for 10 minutes at 10° C. The pellet was washed thrice with 1 ml of the PBS buffer (pH 7.4) to remove any excess antibody. The supernatant was collected to determine the amount of the unconjugated HER-2 protein by comparing to the standard plot. A standard calibration plot for HER-2 was obtained by varying the concentration in the range of 1.25-10 µg/ml using Bio-Rad protein assay kit (Braford method) through measuring the absorbance at 595 nm using spectrophotometer Cary-100. The percentage of the conjugated HER-2 was obtained using the following expression: the percentage of HER-2 conjugated=(the total amount of HER-2 added–the amount of the unconjugated HER2 present in the supernatant)×100. The results indicated that over 70% of the HER-2 antibodies were conjugated to the GMO-MENs' surface.

Figure 16:
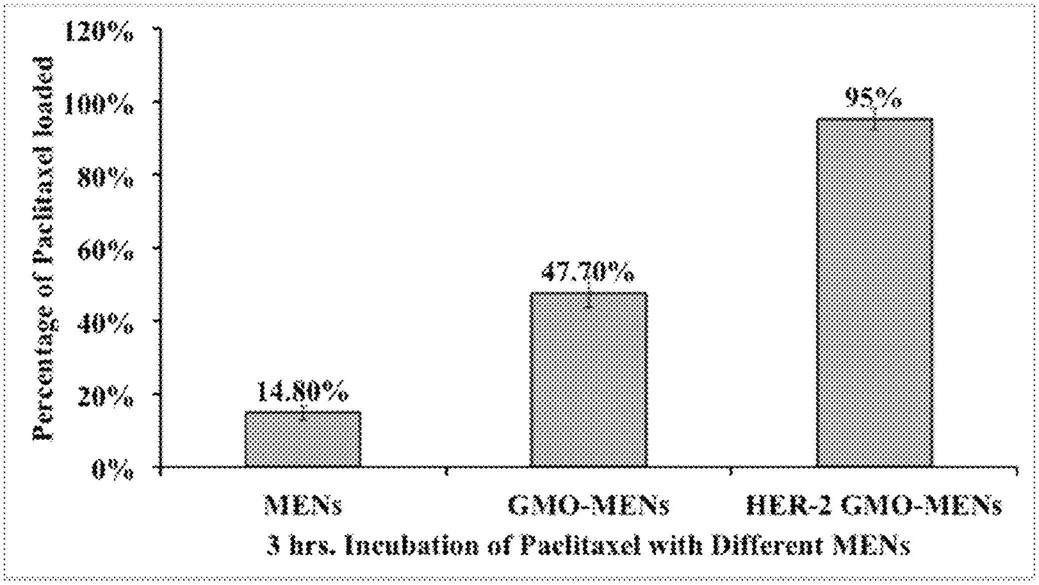
FIG. 16 shows PTX drug loading percentages. PTX drug loading percentage for MENs, GMO-MENs and HER-2-GMO-MENs after 3 hrs. incubation (n=3).

Preparation of PTX-MENs, PTX-GMO-MENs and PTX-HER-2-GMO-MENs:

After 50 µg of PTX drug was added to the solution of 900 µl of the modified PBS (MPBS) buffer and 100 µl of the desired MEN combination (i.e., MENs, GMO-MENs, and HER-2-GMO-MENs at a 5 mg/ml concentration), the solution was incubated for 3 hours while stirred slowly to obtain uniform binding. Then, the solution was centrifuged at 14,000 rpm for 10 minutes at 10° C. to remove any unbounded drug. The supernatant was isolated and absorbance was measured spectrophometrically at 230 nm using Cary-100 UV-VIS spectrophotometer. The PTX loading percentage is shown in FIG. 16. A standard calibration plot for PTX was obtained by varying the drug concentration from 5 to 80 µg in 1 ml of the MPBS solution and the absorbance was measured at 230 nm.

Cell Culture Experiments:

Cell culture experiments were performed using human ovarian carcinoma cell line (SKOV-3) purchased from American Type Culture Collection (Manassas, Va.) and were cultured in McCoy's 5A medium (Life Technologies, NY) supplemented with 10% fetal bovine serum (Sigma-Alrich) and 1% penicillin-streptomycin (science-cell). Human Ovarian Microvasicular endothelial cells (HOMEC) from ScienceCell (Carlsbad, Calif.) and were cultured in endothelial cell medium with endothelial cell growth supplement (1%), fetal bovine serum (5%), and penicillin-streptomycin (1%). All the cells were cultured at 37° C. cell incubator with a 5% $CO_2$ and humidified atmosphere.

Fluorescence Measurements and Confocal Imaging of Drug Uptake by SKOV-3 Cells for Different Drug-Carrier Combinations:

Cellular drug uptake measurements and fluorescence imaging were performed using an Oregon Green® 488 paclitaxel (also called Flutax-2). The experiments were performed in dark. For the fluorescence measurements, the SKOV-3 cells were cultured in 24-well plate at a density of $2\times10^5$ cell per well. After 24-hour incubation at 37° C., the cell medium was replaced with 1 ml/well of the medium containing either one of the four desired drug forms. The concentration of Flutax-2 was normalized to 0.75 μM (1.76 μg/ml) for all the combinations. The cell culture plate was returned to the incubator and incubated for 10 hours. In addition, a set of controls containing no drug for all the combinations was cultured under similar conditions. The cell culture plates containing the Flutax-2-MNs and Flutax-2-GMO-MENs were kept under a 30-Oe field. Upon completion of the 10-hour incubation process, the cells were removed from incubator and the cell culture medium was discarded. The cells were washed with ice-cold PBS buffer thrice. Then, 1 ml of dimethyl sulfoxide (DMSO) was added to each well and incubated for 2 hours at 37° C. After two hours, a rubber policeman was used to ensure the complete removal of the attached cells. The solution was centrifuged at 14,000 rpm for 10 minutes at 4° C. to obtain the cell lysate. The cell lysate along with the in-taken Flutax-2-GMO-MENs was collected and measured for the fluorescence of Flutax-2 (using BioTek instruments, synergy HT) at $\lambda_{ex}$=496 nm and $\lambda_{em}$=524 nm to determine the concentration. All the fluorescence measurements were recorded by subtracting the corresponding controls to adjust the background fluorescence from the cellular components. The protein content of the cell lysate was determined using Bio-Rad protein assay kit (Braford method) by measuring the absorbance at 595 nm using a Cary 100 UV-VIS spectrophotometer.

As for the imaging studies, the cells were cultured on glass cover slips ($1\times1$ in$^2$) pre-coated with the poly-L-Lysine (used as a cell adhesion promoter) in a 6-well cell culture plate at a density of $5\times10^4$ were cultured and let rested for about 10 minutes. Then, 2 ml of Cell medium was added along the walls of the wells. The cell culture plate was incubated for 24 hours at 37° C. The cells were supplied with the fresh cell medium that contained either of the four drug forms under study normalized to the 0.75 μM (1.76 μg/ml) of Flutax-2 concentration. The cell plate containing the Flutax-2-GMO-MENs was kept under a 30-Oe magnetic field. The cell plates were incubated for 10 hours at 37° C. After the incubation process, cover slips were washed three times with the PBS buffer and fixed with 4% paraformaldehyde for 30 minutes followed by washing thrice with the PBS buffer. The cover slips were mounted onto a glass slide using a mounting medium (ProLong Gold Antifade Reagent). The excess mounting medium was removed by placing a small piece of Whatman paper around the edges. After the samples were dried for 2 hours, they were imaged through confocal microscopy (TCS SP2, Leica Microsystems, Germany) at 488 nm (100%) illusion of an argon-ion laser using 60× oil immersion objectives with a high numeric aperture and 1× confocal electronic zoom settings to visualize cells.

What is claimed:

1. A method of treating a subject, comprising:
- administering to the subject a plurality of magneto-electric nanoparticles (MENP) having a drug associated thereto; and
- applying a magnetic field to the subject to generate electric fields on membranes of cells to which the plurality of MENP are adjacent such that the magnetic field strength is sufficient to generate an electric field capable of causing nano-electroporation sites to develop on targeted disease cells but not strong enough to cause nano-electroporation sites on other cells.

2. The method of claim 1, wherein the strength of the magnetic field is increased after nano-electroporation sites are formed on the targeted disease cells in order to release the drug from the plurality of MENP.

3. The method of claim 1, wherein each of the plurality of MENP further comprise a biomarker-specific antibody.

4. The method of claim 1, wherein the drug is an anti-neoplastic drug.

5. The method of claim 1, wherein the disease cells comprise cancer cells.

6. The method of claim 2, wherein the strength of the magnetic field to cause nano-electroporation sites to develop on targeted disease cells, has a value denoted by $H_{th}$, and the strength of the magnetic field in order to release the drug from the MENP, has a value denoted by Hr, and Hr>$H_{th}$, wherein $H_{th}$ is determined by electric properties of cell membrane of the targeted disease cells that lead to localized electroporation effects.

7. The method of claim 6, further comprising adding intermediate layers or coatings between the drug and the MENP to control the Hr.

8. The method of claim 7, wherein Hr has a value between 10 Oe to 200 Oe.

9. The method of claim 1, wherein the magnetic field directs the plurality of MENP adjacent to the targeted disease cells.

10. A method as defined in claim 1, wherein the magnetic field comprises a direct current (DC) field.

11. A method as defined in claim 1, wherein the plurality of MENP comprise $CoFe_2O_4$@$BaTiO_3$.

12. A method for treating diseased cells in a human subject, comprising:
- administering to the subject a plurality of magneto-electric nanoparticles (MENP) having a drug associated thereto;
- applying a magnetic field to the subject to generate electric fields on membranes of cells to which the plurality of MENP are adjacent whereas the strength of the magnetic field is such that it generates an electric field strong enough to cause nano-electroporation sites to develop on the targeted disease cells but not strong enough to cause nano-electroporation sites on other cells; and
- applying a magnetic field equal to or greater than a release field threshold after nano-electroporation sites have developed in order to release the drug from the plurality of MENPs.

13. A method as defined in claim 12, wherein the magnetic field used to develop the nano-electroporation sites on the targeted disease cells comprises a direct current (DC) field.

14. A method as defined in claim 13, wherein the magnetic field used to release the drug from the MENP comprises an alternating current (AC) field.

15. A method as defined in claim 12, wherein the magnetic field used to release the drug from the MENP comprises an alternating field.

16. A method as defined in claim 12, where the magnetic field used to release the drug from the MENP is stronger than the magnetic field for nano-electroporation.

* * * * *